(12) United States Patent
LoVetri et al.

(10) Patent No.: US 10,197,508 B2
(45) Date of Patent: Feb. 5, 2019

(54) IMAGING USING RECONFIGURABLE ANTENNAS

(71) Applicant: UNIVERSITY OF MANITOBA, Winnipeg (CA)

(72) Inventors: Joe LoVetri, Winnipeg (CA); Mohammad Asefi, Winnipeg (CA)

(73) Assignee: UNIVERISTY OF MANITOBA (CA)

( * ) Notice: Subject to any disclaimer, the term of this patent is extended or adjusted under 35 U.S.C. 154(b) by 9 days.

(21) Appl. No.: 15/324,196

(22) PCT Filed: Jul. 7, 2015

(86) PCT No.: PCT/IB2015/055142
§ 371 (c)(1),
(2) Date: Jan. 5, 2017

(87) PCT Pub. No.: WO2016/005909
PCT Pub. Date: Jan. 14, 2016

(65) Prior Publication Data
US 2017/0199134 A1 Jul. 13, 2017

Related U.S. Application Data

(60) Provisional application No. 62/021,593, filed on Jul. 7, 2014.

(51) Int. Cl.
*H01L 21/00* (2006.01)
*G01N 22/00* (2006.01)
(Continued)

(52) U.S. Cl.
CPC ........... *G01N 22/00* (2013.01); *A61B 5/0507* (2013.01); *A61B 5/0536* (2013.01); *A61B 5/708* (2013.01);
(Continued)

(58) Field of Classification Search
CPC ....... H01L 21/00; H01L 2221/00; G06T 1/00; G06T 2200/00; H04W 4/00; G08B 1/00;
(Continued)

(56) References Cited

U.S. PATENT DOCUMENTS 5,051,748 A 9/1991 Pichot et al.
5,430,369 A 7/1995 Blomey et al.
(Continued)

FOREIGN PATENT DOCUMENTS

CA 2 191 312 A1 12/1995
CA 2 585 073 A1 5/2006
(Continued)

OTHER PUBLICATIONS

Abubakar et al., "2.5d forward and inverse modeling for interpreting low frequency electromagnetic measurements," Jul.-Aug. 2008, *Geophysics*, 73(4):F165-77.
(Continued)

*Primary Examiner* — Jermele M Hollington
*Assistant Examiner* — Temilade Rhodes-Vivour
(74) *Attorney, Agent, or Firm* — Mueting, Raasch & Gebhardt, P.A.

(57) ABSTRACT

Exemplary imaging systems, apparatus, and methods may include a plurality of reconfigurable antenna assemblies. The reconfigurable antenna assemblies may each include one or more antennas. The antennas may be configured in a plurality of states including a passive state in which the antenna may not perturb the electromagnetic field. The antennas may be positioned about a measurement domain such as, e.g., a conductive measurement chamber.

33 Claims, 30 Drawing Sheets

(51) Int. Cl.
*A61B 5/05* (2006.01)
*A61B 5/053* (2006.01)
*G06T 1/00* (2006.01)
*H04W 4/00* (2018.01)
*A61B 5/00* (2006.01)

(52) U.S. Cl.
CPC ..... *A61B 5/7267* (2013.01); *A61B 2560/0223* (2013.01); *A61B 2562/00* (2013.01); *A61B 2562/0228* (2013.01); *A61B 2562/04* (2013.01); *G06T 1/00* (2013.01); *H01L 2221/00* (2013.01); *H04W 4/00* (2013.01)

(58) Field of Classification Search
CPC ........ G09G 1/00; G09G 2230/00; H04L 1/00; H04L 2201/00
See application file for complete search history.

(56) References Cited

U.S. PATENT DOCUMENTS

| | | | |
|---|---|---|---|
| 5,627,553 | A | 5/1997 | Poulton |
| 5,704,355 | A | 1/1998 | Bridges |
| 5,715,819 | A | 2/1998 | Svenson et al. |
| 5,829,437 | A | 11/1998 | Bridges |
| 5,999,836 | A | 12/1999 | Nelson et al. |
| 6,061,589 | A | 5/2000 | Bridges et al. |
| 6,275,045 | B1 | 8/2001 | Eloy |
| 6,332,087 | B1 | 12/2001 | Svenson et al. |
| 6,448,788 | B1 | 9/2002 | Meaney et al. |
| 6,490,471 | B2 | 12/2002 | Svenson et al. |
| 6,762,709 | B2 * | 7/2004 | Kikuchi ............... G01V 8/005 342/174 |
| 6,777,684 | B1 | 8/2004 | Volkov et al. |
| 6,885,191 | B1 | 4/2005 | Gleman |
| 6,965,340 | B1 | 11/2005 | Baharav et al. |
| 7,167,133 | B2 | 1/2007 | Nagashima |
| 7,439,736 | B2 | 10/2008 | Meaney et al. |
| 7,746,266 | B2 | 6/2010 | Zoughi et al. |
| 7,825,667 | B2 | 11/2010 | Fang et al. |
| 7,843,347 | B2 | 11/2010 | Nikitin et al. |
| 8,724,864 | B2 | 5/2014 | Persson et al. |
| 2004/0077943 | A1 | 4/2004 | Meaney |
| 2005/0104603 | A1* | 5/2005 | Peschmann .......... G01V 5/0016 324/637 |
| 2005/0107692 | A1 | 5/2005 | Li et al. |
| 2006/0239404 | A1 | 10/2006 | Upda et al. |
| 2006/0293597 | A1 | 12/2006 | Johnson et al. |
| 2007/0015993 | A1 | 1/2007 | Ciocan et al. |
| 2011/0040176 | A1 | 2/2011 | Razansky et al. |
| 2011/0137381 | A1 | 6/2011 | Lee et al. |
| 2011/0227586 | A1* | 9/2011 | Lovetri ............... A61B 5/0507 324/637 |
| 2012/0191148 | A1 | 7/2012 | McKenna et al. |
| 2012/0330151 | A1 | 12/2012 | Weinstein et al. |
| 2014/0276031 | A1* | 9/2014 | Lomnitz ............. A61B 5/7214 600/430 |
| 2015/0201838 | A1* | 7/2015 | Gencer ................ A61B 5/0051 600/430 |

FOREIGN PATENT DOCUMENTS

| | | |
|---|---|---|
| CA | 2 885 890 A1 | 3/2014 |
| EP | 0 928 157 B1 | 7/1999 |
| WO | WO 2009/066186 A2 | 5/2009 |
| WO | WO 2009/066186 A3 | 7/2009 |
| WO | WO 2010/049253 A1 | 5/2010 |
| WO | WO 2013/005134 A2 | 1/2013 |
| WO | WO 2015/101921 A1 | 7/2015 |

OTHER PUBLICATIONS

Abubakar et al., "A multiplicative regularization approach for deblurring problems," Nov. 2004, *IEEE Transactions on Image Processing*, 13(11):1524-32.

Abubakar et al., "A robust iterative method for Born inversion," Feb. 2004, *IEEE Transactions on Geoscience and Remote Sensing*, 42(2):342-54.

Abubakar et al., "Imaging of biomedical data using a multiplicative regularized contrast source inversion method," 2002, *IEEE Trans. Microw. Theory Tech.*, 50(7):1761-71.

Abubakar et al., "Iterative forward and inverse algorithms based on domain integral equations for three-dimensional electric and magnetic objects," 2004, *Journal of Computational Physics*, 195(1):236-62.

Abubakar et al., "Non-linear three-dimensional inversion of cross-well electrical measurements," 2000, *Geophysical Prospecting*, 48(1):109-134.

Abubakar et al., "The contrast source inversion method for location and shape reconstructions," 2002, *Inverse Problems*, 18:495-510.

Bolomey et al., *Engineering Applications of the Modulated Scatterer Technique*. Artech House, Inc.: Norwood, Massachusetts; 2001. Cover Page, Publisher's Page, and Table of Contents.

Bolomey et al., "On the possible use of microwave-active imaging for remote thermal sensing," Sep. 1983, *IEEE Transactions on Microwave Theory and Techniques*, 31(9):777-81.

Broquetas et al., "Cylindrical geometry: a further step in active microwave tomography," May 1991, *IEEE Transactions on Microwave Theory and Techniques*, 39(5):836-44.

Bulyshev et al., "Three-dimensional microwave tomography. Theory and computer experiments in scalar approximation," Jun. 2000, *Inverse Problems*, 16(3): 863-75.

Caorsi et al. "A passive antenna system for data acquisition in scattering applications". 2002. *IEEE Antennas and Wireless Propagation Letters*, 1:203-06.

Charbonnier et al., "Deterministic Edge-Preserving Regularization in Computed Imaging," Feb. 1997, *IEEE Transactions on Image Processing*, 6(2): 298-311.

Chew et al. "Reconstruction of two-dimensional permittivity distribution using the distorted born iterative method" Jun. 1990. *IEEE Transactions on Medical Imaging*, 9(2):218-25.

Crocco et al., "On embedded microwave imaging systems: retrievable information and design guidelines," Mar. 27, 2009, *Inverse Problems*, 25(6): 065001 (17 pgs).

Cullen et al. "A new perturbation method for measuring microwave fields in free space," Nov. 1955. *Proceedings of the IEE—Part B: Radio and Electronic Engineering*. 102(6):836-44.

De Zaeytijd et al. "Full-wave three-dimensional microwave imaging with a regularized Gauss-Newton method theory and experiment," Nov. 2007. *IEEE Transactions on Antennas and Propagation*, 55(11):3279-92.

Fang et al. "Viable three-dimensional medical microwave tomography: theory and numerical experiments," Feb. 1, 2010, *IEEE Transactions Antennas and Propagation*, 58(2):449-58.

Fear et al., "Enhancing Breast Tumor Detection with Near-Field Imaging," Mar. 2002, *IEEE Microwave Magazine*, 48-56.

Fear et al. "Microwave Detection of Breast Cancer," Nov. 2000, *IEEE Transactions on Microwave Theory and Techniques*, 48(11): 1854-63.

Fhager et al., "Reconstruction quality and spectral content of an electromagnetic time-domain inversion algorithm," Aug. 2006, *IEEE Transactions on Biomedical Engineering*, 53(8):1594-04.

Franchois et al., "Quantitative microwave imaging with a 2.45-GHz planar microwave camera," Aug. 1998, *IEEE Transactions on Medical Imaging*, 17(4): 550-61.

Franchois et al., "A quasi-Newton reconstruction algorithm for a complex microwave imaging scanner environment,"Jan. 10, 2003, *Radio Science*, 38(2):8011-23.

Franza et al., "SICS: A sensor interaction compensation scheme for microwave imaging," Feb. 2002, *IEEE Transactions on Antennas and Propagation*, 50(2): 211-16.

Geffrin et al., "Continuing with the Fresnel database: experimental setup and improvements in 3D scattering measurements," 2009, *Inverse Problems*, 25:024001.

(56) References Cited

OTHER PUBLICATIONS

Ghasr et al. "A novel 24 GHz one-shot, rapid and portable microwave imaging system." (*IEEE Instrumentation and Measurement Technology Conference*) Victoria, Vancouver Island, Canada, May 12-15, 2008, 1798-1802.
Ghasr et al. "Portable real-time microwave camera at 24 GHz," Feb. 2012, *IEEE Transactions on Antennas and Propagation*, 60(2): 1114-25.
Gilmore et al., "A study of matching fluid loss in a biomedical microwave tomography system," Feb. 2013, *Medical Physics*, 40(2):023101.
Gilmore et al., "A wideband microwave tomography system with a novel frequency selection procedure," Apr. 2010, *IEEE Transactions on Biomedical Engineering*, 57(4):894-904.
Gilmore et al., "Corrections to the 'Enhancement of microwave tomography through the use of electrically conducting enclosures,'" Jan. 2010, *Inverse Problems*, 26(1):019801 (7 pgs.).
Gilmore et al., "Enhancement of microwave tomography through the use of electrically conducting enclosures," Apr. 8, 2008, *Inverse Problems*, 24(3):035008 (21 pgs).
Gilmore et al., "Microwave Biomedical Data Inversion Using the Finite-Difference Contrast Source Inversion Method," May 2009, *IEEE Transactions on Antennas Propagation*, 57(5):1528-38.
Gilmore et al., "On super-resolution with an experimental microwave tomography system," 2010. *IEEE Antennas and Wireless Propagation Letters*, 9:393-96.
Gilmore et al., "The University of Manitoba Microwave Imaging Repository: A Two-Dimensional Microwave Scattering Database for Testing Inversion and Calibration Algorithms," Oct. 2011, *IEEE Antennas and Propagation Magazine*, 53(5):126-133.
Habashy et al., "A general framework for constraint minimization for the inversion of electromagnetic measurements," 2004, *Progress in Electromagnetics Research*, 46: 265-312.
Halter et al. "The correlation of *in vivo* and *ex vivo* tissue dielectric properties to validate electromagnetic breast imaging: initial clinical experience," 2009, *Physiological Measurement*, 30:S121-36.
Harrington. "Small resonant scatterers and their use for field measurements," 1962. *IRE Transactions on Microwave Theory and Techniques*, 10(3):165-74.
Harrington. *Time-Harmonic Electromagnetic Fields*. Dudley (Ed.) John Wiley & Sons, Inc.: New York. May 1962. Cover Page, Copyright Page, Table of Contents, Preface.
Henriksson et al., "Quantitative microwave imaging for breast cancer detection using a planar 2.45 GHz system," Oct. 2010. *IEEE Transactions on Instrumentation and Measurment*, 59(10):2691-99.
International Patent Application No. PCT/IB2014/067390, filed Dec. 29, 2014; International Search Report / Written Opinion dated May 5, 2015; 11 pages.
International Patent Application No. PCT/IB2014/067390, filed Dec. 29, 2014; International Preliminary Report on Patentability dated Jul. 14, 2016; 7 pages.
International Patent Application No. PCT/IB2015/055142, filed Jul. 7, 2015; International Search Report / Written Opinion dated Nov. 3, 2015; 12 pages.
International Patent Application No. PCT/IB2015/055142, filed Jul. 7, 2015; International Preliminary Report on Patentability dated Jul. 7, 2014; 9 pages.
Joachimowicz et al., "Inverse Scattering: An Iterative Numerical Method for Electromagnetic Imaging," Dec. 1991, *IEEE Transactions on Antennas and Propagation*, 39(12):1742-53.
Kleinman et al., "A Modified gradient method for two-dimensional problems in tomography," 1992, *Journal of Computational and Applied Mathematics*, 42(1):17-35.
Klemm et al., "Radar-Based Breast Cancer Detection Using a Hemispherical Antenna Array—Experimental Results," Jun. 2009, *IEEE Transactions on Antennas and Propagation*, 57(6):1692-1704.
Lazebnik et al., "Highly Accurate Debye Models for Normal and Malignant Breast Tissue Dielectric Properties at Microwave Frequencies," Dec. 2007, *IEEE Microwave and Wireless Components Letters*, 17(12):822-24.
Lencrerot et al., "Imposing Zernike representation for imaging two-dimensional targets," Feb. 3, 2009, *Inverse Problems in Science and Engineering*, 25(3):035012 (21 pgs).
Lencrerot et al., "Measurement strategies for a confined microwave circular scanner," Sep. 2009, *Inverse Problems in Science and Engineering*, 17(6):787-802. [Available online Aug. 6, 2009].
LoVetri, Joe, "Computational electromagnetics and electromagnetic inverse imaging," Grant Abstract [online]. Natural Sciences and Engineering Research Council of Canada, project dates: fiscal year 2010-2011 [retrieved on August 9, 2011]. Retrieved from the Internet: <:http://www.outil.ost.uqam.ca/CRSNG/Detail.aspx?Cle=451511&Langue=2>; 2 pgs.
Meaney et al., "A clinical prototype for active microwave imaging of the breast," Nov. 2000, *IEEE Transactions on Microwave Theory and Techniques*, 48(11):1841-53.
Meaney et al., "Initial clinical experience with microwave breast imaging in women with normal mammography," Feb. 2007,*Acad. Radial.*, 14(2):207-18.
Meaney et al., "Microwave imaging for tissue assessment: initial evaluation in multitarget tissue-equivalent phantoms," Sep. 1996, *IEEE Transactions on Biomedical Engineering*, 43(9):878-90.
Meaney et al., "Nonactive antenna compensation for fixed-array microwave imaging: Part II—Imaging results," Jun. 1999, *IEEE Transactions on Medical Imaging*, 18(6):508-18.
Meaney et al., "Pre-scaled two-parameter Gauss-Newton image reconstruction to reduce property recovery imbalance," 2002, *Physics in Medicine and Biology*, 47(7):1101-19.
Memarzadeh-Tehran et al., "Optically modulated probe for precision near-field measurements," 2010. *IEEE Transactions on Instrumentation and Measurement*, 59(10):2755-62.
Mohassel, "Meander antennas". Ph.D. Dissertation. The University of Michigan. 1982.
Mojabi et al., "A Multiplicative Regularized Gauss-Newton Inversion for Shape and Location Reconstruction," Dec. 2011, *IEEE Transactions on Antennas and Propagation*, 59(12):4790-4802.
Mojabi et al., "A Novel Microwave Tomography System Using a Rotatable Conductive Enclosure," *IEEE Transactions on Antennas and Propagation*, May 2, 2011; 59(5): 1597-1605. Available online Mar. 7, 2011.
Mojabi et al., "Adapting the Normalized Cumulative Periodogram Parameter-Choice Method to the Tikhonov Regularization of 2-D/TM Electromagnetic Inverse Scattering Using Born Iterative Method," 2008, *Progress in Electromagnetics Research M*, 1:111-38.
Mojabi et al., "Biomedical microwave inversion in conducting cylinders of arbitrary shapes," *13th International Symposium on Antenna Technology and Applied Electromagnetics and the Canadian Radio Science Meeting(ANTEM/URSI)*, Toronto, Ontario, Feb. 15-18, 2009: 1-4.
Mojabi et al., "Comparison of TE and TM Inversions in the Framework of the Gauss-Newton Method," Apr. 2010, *IEEE Transactions on Antennas Propagation*, 58(4): 1336-48.
Mojabi et al., "Eigenfunction contrast source inversion for circular metallic enclosures," Feb. 2010, *Inverse Problems*26(2): 025010 (23 pgs.).
Mojabi et al., "Enhancement of the Krylov subspace regularization for microwave biomedical imaging," Dec. 2009,*IEEE Transactions on Medical Imaging*, 28(12):2015-19. Available online Jul. 24, 2009.
Mojabi et al., "Microwave Biomedical Imaging Using the Multiplicative Regularized Gauss-Newton Inversion," 2009, *IEEE Antennas and Wireless Propagation Letters*, 8:645-48.
Mojabi et al. "Overview and classification of some regularization techniques for the Gauss-Newton inversion method applied to inverse scattering problems," Sep. 2009, *IEEE Transactions on Antennas and Propagation*, 57(9):2658-65.
Nikolova, "Microwave Imaging for Breast Cancer," Dec. 2011, *IEEE Microwave Magazine*, 12(7):78-94.

(56) References Cited

OTHER PUBLICATIONS

O'Halloran et al., "Rotating Antenna Microwave Imaging System for Breast Cancer Detection," 2010, *Progress in Electromagnetics Research*, 107:203-17.
Ostadrahimi et al., "A modified double layer tapered slot antenna with improved cross polarization" 2009. *13th International Symposium on Antenna Technology and Applied Electromagnetics and the Canadian Radio Sciences Meeting.* IEEE.
Ostadrahimi et al., "A Multiprobe-Per-Collector Modulated Scatterer Technique for Microwave Tomography," 2011, *IEEE Antennas and Wireless Propagation Letters*, 10:1445-48.
Ostadrahimi et al., "An MST-based microwave tomography system using homodyne receiver," 2013, *IEEE International Symposium on Antennas and Propagation and USNC/URSI National Radio Science Meeting.* IEEE. pp. 1-4.
Ostadrahimi et al., "A Near-Field Dual Polarized (TE-TM) Microwave Imaging System," Mar. 2013, *IEEE Transactions on Microwave Theory and Techniques*, (61)3:1376-84.
Ostadrahimi et al., "A Novel Microwave Tomography System Based on the Scattering Probe Technique," Feb. 2012, *IEEE Transactions on Instrumentation and Measurement*, 61(2):379-90.
Ostadrahimi et al., "Analysis of Incident Field Modeling and Incident/Ccattered Field Calibration Techniques in Microwave Tomography," 2011, *IEEE Antennas and Wireless Propagation Letters*, 10:900-03.
Ostadrahimi et al., "Enhancement of Gauss-Newton Inversion Method for Biological Tissue Imaging," Sep. 2013, *IEEE Transactions on Microwave Theory and Techniques*, 61(9):3424-34.
Ostadrahimi et al. "Investigating a double layer Vivaldi antenna design for fixed array field measurement". 2010. *Intl. Journal of Ultra Wideband Communications and Systems.* 1(4):282-290.
Ostadrahimi et al., "Slotted Waveguide Arrays for Collecting Near-Field Scattering Data" 2014, University of Manitoba—CancerCare Manitoba & Department of Physics and Astronomy, 1-2.
Pastorino, *Microwave Imaging.* John Wiley & Sons: Hoboken, New Jersey; 2010. Title Page, Copyright Page, Table of Contents, and Introduction, pp. 1-4.
Pastorino, "Stochastic Optimization Methods Applied to Microwave Imaging: A Review," Mar. 2007, *IEEE Transactions on Antennas and Propagation*, 55(3):538-48.
Paulsen et al., "Nonactive antenna compensation for fixed-array microwave imaging—Part I: Model development," Jun. 1999, *IEEE Transactions on Medical Imaging*, 18(6):496-507.
Rubæk et al., "Computational Validation of a 3-D Microwave Imaging System for Breast-Cancer Screening," Jul. 2009, *IEEE Transactions on Antennas and Propagation*, (57)7:2105-15.
Rubaek et al., "Nonlinear Microwave Imaging for Breast-Cancer Screening Using Gauss-Newton's Method and the CGLS Inversion Algorithm," Aug. 2007, *IEEE Transactions on Antennas and Propagation*, 55(8): 2320-31.
Semenov et al., "Microwave tomography: review of the progress towards clinical applications," 2009. *Philosophical Transactions of the Royal Society*, 367:3021-42.
Semenov et al., "Microwave tomography of extremities: 1. dedicated 2D system and physiological signatures," Apr. 7, 2011, *Physics in Medicine and Biology*, 56(7):2005-17.
Semenov et al. "Microwave-tomographic imaging of the high dielectric-contrast objects using different image-reconstruction approaches," Jul. 2005, *IEEE Transactions on Microwave Theory and Techniques*, 53(7):2284-94.
Semenov et al., "Spatial resolution of microwave tomography for detection of Myocardial Ischemia and infarction—experimental study on two-dimensional models," Apr. 2000. *IEEE Transactions on Microwave Theory and Techniques*, 48(4):538-44.
Semenov et al., "Three-dimensional microwave tomography: initial experimental imaging of animals," Jan. 2002, *IEEE Transactions on Biomedical Engineering*, 49(1):55-63.
Stang et al., "A preclinical system prototype for focused microwave thermal therapy of the breast," Sep. 2012, *IEEE Transactions on Biomedical Engineering*, 59(9):2431-38.
Tijhuis et al., "Theoretical and Computational Aspects of 2-D Inverse Profiling," Jun. 2001, *IEEE Transactions on Geoscience and Remote Sensing*, 39(6):1316-30.
Van Den Berg et al., "A contrast source inversion method," 1997, *Inverse Problems*, 13(6):1607-20.
Vardalahos, "Investigation of Loaded Monopole Antenna," Ph.D. Dissertation. University of Leeds. 2000.
Wadbro et al., "Microwave Tomography Using Topology Optimization Techniques," Mar. 2008, *SIAM J Sci. Comput.*, 30(3):1613-33.
Wang et al., "An iterative solution of the two-dimensional electromagnetic inverse scattering problem," 1989, *Int. J. Imag. Syst. Technol.*, 1(1):100-08. Available online Oct. 20, 2005.
Yu et al., "Active Microwave Imaging II: 3-D System Prototype and Image Reconstruction From Experimental Data," Apr. 2008, *IEEE Transactions on Microwave Theory and Techniques*, 56(4):991-1000.
Zaeytijd et al., "Full-Wave Three-Dimensional Microwave Imaging With a Regularized Gauss-Newton Method—Theory and Experiment," Nov. 2007, *IEEE Transactions on Antennas and Propagation*, 55(11):3279-92.
Zakaria et al., "Application of multiplicative regularization to the finite-element contrast source inversion method," Sep. 2011, *IEEE Transactions on Antennas and Propagation*, 59(9):3495-98.
Zakaria et al., "Finite-element contrast source inversion method for microwave imaging," 2010, *Inverse Problems*, 26:115010.
Zakaria et al., "The Finite-Element Method Contrast Source Inversion Algorithm for 2D Transverse Electric Vectorial Problems," Oct. 2012, *IEEE Transactions on Antennas and Propagation*, 60(10):4757-65.
Zakaria et al., "Full-vectorial parallel finite-element contrast source inversion method," 2013, *Progress in Electromagnetics Research*, 142:463-83.

* cited by examiner

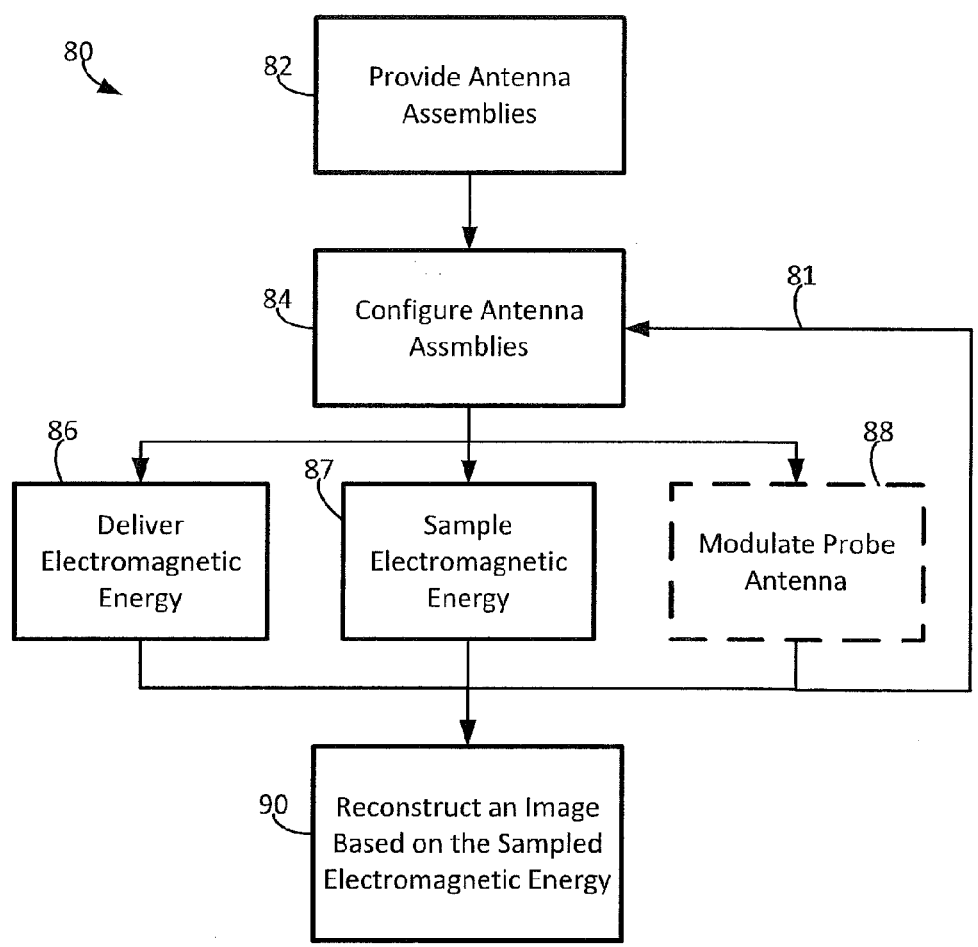

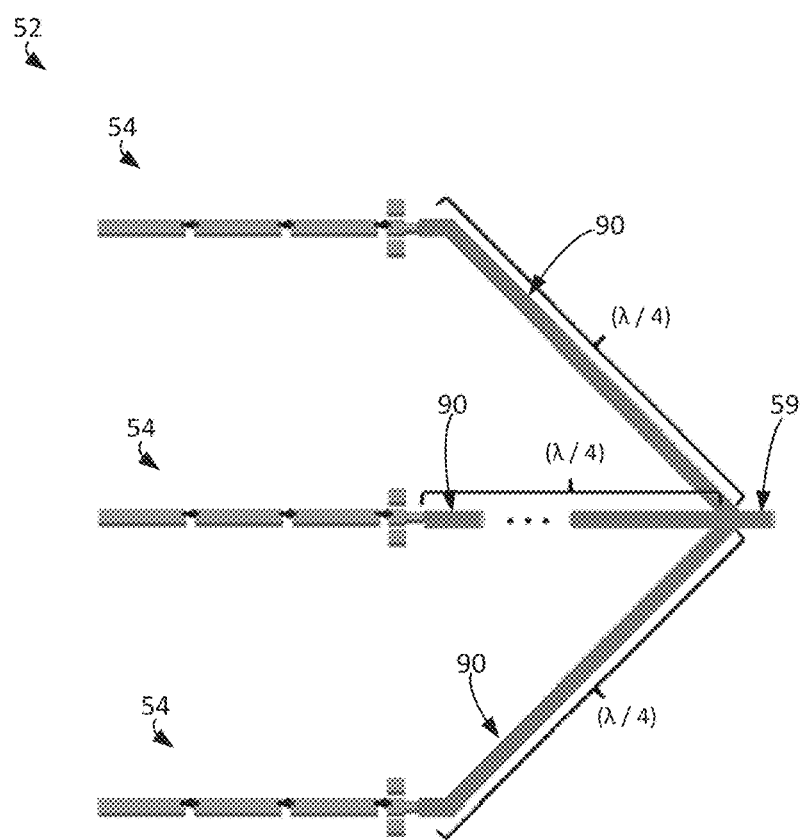

FIG. 8
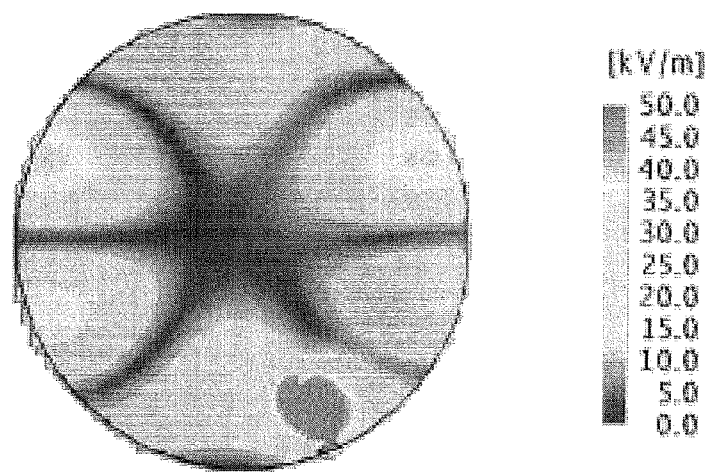
(a)
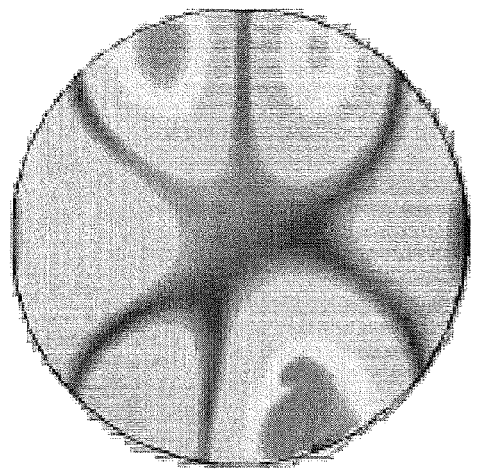
(b)
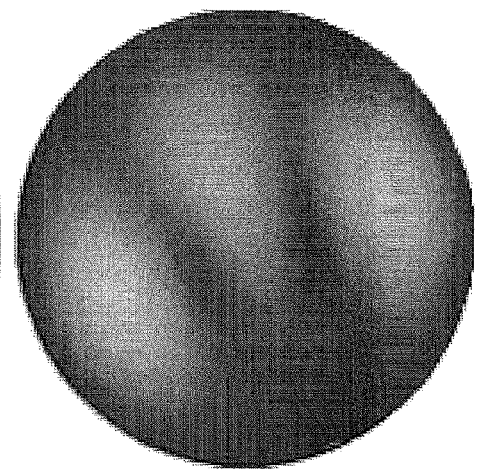
(c)

FIG. 9
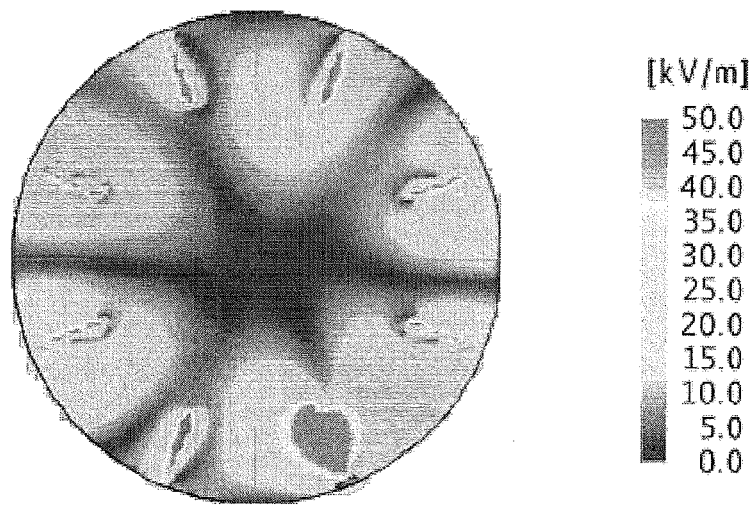
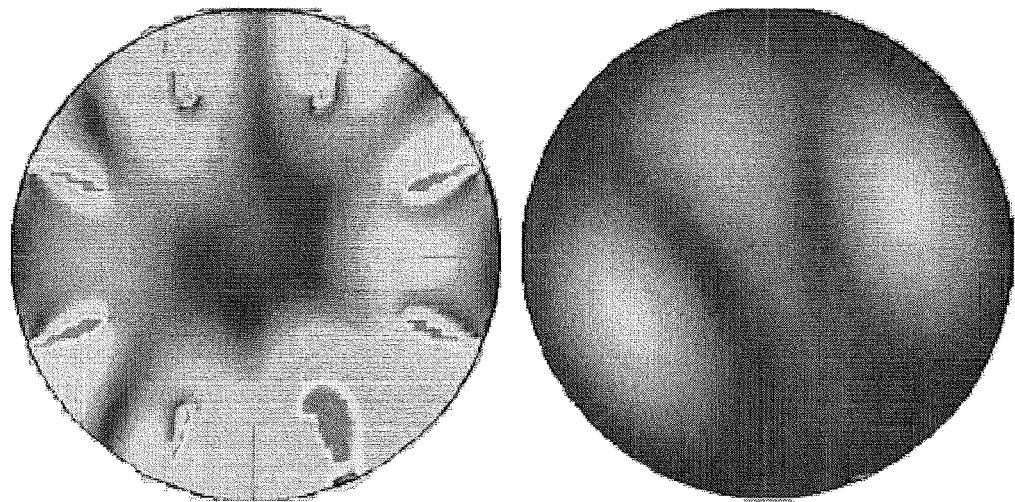

IMAGING USING RECONFIGURABLE ANTENNAS

CROSS-REFERENCE TO RELATED APPLICATION

This application is the § 371 U.S. National Stage of International Application No. PCT/IB2015/055142, filed 2015 Jul. 7, which claims the benefit of U.S. Provisional Application Ser. No. 62/021,593 filed on 2014 Jul. 7 entitled "IMAGING USING RECONFIGURABLE ANTENNAS," which are incorporated herein by reference in their entireties.

The present disclosure pertains to imaging systems and imaging methods, e.g., microwave and millimeter wave energy based imaging, using reconfigurable antenna assemblies.

In the art of microwave imaging (MWI), an object of interest (OI) is illuminated by microwave energy and the scattered fields are collected outside the OI. The collected scattered fields may then be used to reconstruct qualitative, and possibly quantitative images, or interior maps, of the OI that include its location, geometry, shape, magnetic properties, and dielectric properties. The ability to provide quantitative imaging and to utilize non-ionizing radiations associated with MWI make MWI an appropriate candidate for use in many applications such as non-destructive testing in industrial applications, non-invasive imaging of biological tissues, remote sensing, geophysical survey of underground objects, and other security and military applications.

Due to the inherent non-linear and ill-posed behavior of the inverse scattering problem used in MWI, a substantial amount of electromagnetic scattering data may need to be collected in order to ensure a robust inversion and quantitatively-accurate image. The need for more data can be satisfied by several approaches such as, e.g., increasing the number of data acquisition points, using different frequencies, collecting multiple field polarizations, etc.

Microwave imaging has been deployed in many biomedical, security, and industrial applications such as breast cancer diagnostics (see, e.g., N. Nikolova, "Microwave imaging for breast cancer," Microwave Magazine, IEEE, vol. 12, no. 7, pp. 78-94, December 2011), biological tissue imaging (see, e.g., M. Ostadrahimi, P Mojabi, A. Zakaria, J. LoVetri, and L. Shafai, "Enhancement of Gauss-Newton inversion method for biological tissue imaging," Microwave Theory and Techniques, IEEE Transactions on, vol. 61, no. 9, pp. 3424-3434, 2013), non-destructive testing and evaluation (see, e.g., R. Zoughi, M. A. AbouKhousa, M. T. A. Ghasr, S. Kharkivskiy, and D. Pommerenke, "Microwave and millimeter wave imaging system," patent, U.S. Pat. No. 7,746,266; and M. Ghasr, M. Abou-Khousa, S. Kharkovsky, R. Zoughi, and D. Pommerenke, "Portable real-time microwave camera at 24 GHz," Antennas and Propagation, IEEE Transactions on, vol. 60, no. 2, pp. 1114-1125, February 2012), and geophysical surveying (see, e.g., A. Abubakar and P. Van Den Berg, "Non-linear three-dimensional inversion of cross-well electrical measurements," Geophysical prospecting, vol. 48, no. 1, pp. 109-134, 2000).

The basic operation of a MWI system is based on illuminating an object-of-interest (OI) with electromagnetic energy using a transmitting antenna and collecting the scattered electromagnetic fields at various receiving locations. The collected field data may be calibrated and then processed using non-linear inverse scattering algorithms (see, e.g., Q. Fang, P. Meaney, and K. Paulsen, "Viable three-dimensional medical microwave tomography: theory and numerical experiments," Antennas and Propagation, IEEE Transactions on, vol. 58, no. 2, pp. 449-458, 2010; J. De Zaeytijd, A. Franchois, C. Eyraud, and J. Geffrin, "Full-wave three-dimensional microwave imaging with a regularized Gauss-Newton method theory and experiment," Antennas and Propagation, IEEE Transactions on, vol. 55, no. 11, pp. 3279-3292, 2007; A. Zakaria, C. Gilmore, and J. LoVetri, "Finite-element contrast source inversion method for microwave imaging," Inverse Problems, vol. 26, p. 115010, 2010; and P. Mojabi and J. LoVetri, "Microwave biomedical imaging using the multiplicative regularized Gauss-Newton inversion," Antennas and Wireless Propagation Letters, IEEE, vol. 8, pp. 645-648, 2009) or radar techniques (see, e.g., M. Klemm, I. Craddock, J. Leendertz, A. Preece, and R. Benjamin, "Radar-based breast cancer detection using a hemispherical antenna array experimental results," Antennas and Propagation, IEEE Transactions on, vol. 57, no. 6, pp. 1692-1704, 2009).

Depending on the application, the imaging results, or outcome, may be either a quantitative reconstruction of the complex dielectric and magnetic profile of the OI that provides information on its shape and location and/or a qualitative image that produces the shadow of the OI. Qualitative imaging method may not incur a heavy computational burden (e.g., such as quantitative MWI) and may be accomplished in real-time. Although qualitative imaging may provide some information about the internal structure and composition of an OI, qualitative imagine may not provide the ability to identify materials, such as, e.g., tissues, etc., in a reconstructed image as well as quantitative MWI may be able to provide (e.g. which may be helpful in biomedical and geo-surveying applications). Further, quantitative images can be processed and interpreted by intelligent computer algorithms due to the known values of the dielectric properties of materials and biological tissues, which may accelerate image interpretation by skilled technicians, radiologists, and trained human resources.

In order to obtain a quantitative interior image of an OI, microwave energy should penetrate sufficiently into the object. To reduce reflections from the boundary of the OI, and thus maximize field penetration, the OI may be immersed into a matching fluid (see, e.g., C. Gilmore, A. Zakaria, J. LoVetri, and S. Pistorius, "A study of matching fluid loss in a biomedical microwave tomography system," Medical physics, vol. 40, p. 023101, 2013). Furthermore, because wave penetration depth is inversely proportional to the frequency of operation, upper limits on the frequency that can be used may exist, especially when imaging biological targets. Further, microwave imaging systems used for biomedical applications may operate up to X-band such as, e.g., 915 MHz (see, e.g., J. Stang, M. Haynes, P. Carson, and M. Moghaddam, "A preclinical system prototype for focused microwave thermal therapy of the breast," Biomedical Engineering, IEEE Transactions on, 2012, early access), 1.0-2.3 GHz (see, e.g., S. Semenov, J. Kellam, Y. Sizov, A. Nazarov, T. Williams, B. Nair, A. Pavlovsky, V. Posukh, and M. Quinn, "Microwave tomography of extremities: 1. dedicated 2D system and physiological signatures," Physics in Medicine and Biology, vol. 56, p. 2005, 2011), 2.45 GHz (see, e.g., A. Franchois, A. Joisel, C. Pichot, and J. Bolomey, "Quantitative microwave imaging with a 2.45-GHz planar microwave camera," Medical Imaging, IEEE Transactions on, vol. 17, no. 4, pp. 550-561, 1998), 0.9-1.5 GHz (see, e.g., P. Meaney, M. Fanning, T. Raynolds, C. Fox, Q. Fang, C. Kogel, S. Poplack, and K. Paulsen, "Initial clinical experience with microwave breast imaging in women with normal mammography," Academic Radiology, vol. 14, no. 2, pp.

207-218, 2007), 2-8 GHz (see, e.g., E. C. Fear, M. A. Stuchly, "Microwave Detection of Breast Cancer," Microwave Theory and Techniques, IEEE Transactions on, vol. 48, pp. 1854-1863, November 2000), and/or 4-9 GHz (see, e.g., M. Klemm, I. J. Craddock, J. A. Leendertz, A. Preece, R. Benjamin, "Radar-Based Breast Cancer Detection Using a Hemispherical Antenna Array—Experimental Results," Antennas and Propagation, IEEE Transactions on, vol. 57, no. 6, pp. 1692-1704, June 2009).

Due to the low operational frequency and the compact size of MWI systems, a target may be located in the near-field region of the antennas. In this region, complicated field distributions may exist due to the presence of some or all polarizations, arbitrary wave impedances, and both propagating as well as evanescent modes. Further, polarization may be utilized in microwave imaging and may not be generally available in other imaging modalities. The use of different polarizations in MWI may use inversion algorithms capable of inverting vector field problems, specialized measurement techniques sensitive to individual polarizations, and appropriate calibration techniques. The ability to use arbitrary polarizations of electromagnetic energy may further require full-wave computational models of the imaging chamber (see, e.g., M. Ostadrahimi, P Mojabi, C. Gilmore, A. Zakaria, S. Noghanian, S Pistorius, and J. LoVetri, "Analysis of incident field modeling and incident/scattered field calibration techniques in microwave tomography," Antennas and Wireless Propagation Letters, IEEE, vol. 10, pp. 900-903, 2011). Such full-wave modeling of the imaging system may be computationally expensive. Further, the measurement of different polarizations may use sophisticated experimental systems that can differentiate between measured signal polarizations. Still further, associated calibration techniques for full-wave modeling may need to be tailored for each polarization and for the specific measurement system being used.

In at least one MWI approach, some field measurement probes distributed at various locations may be used to infer the electromagnetic field impinging on their location. By changing/modulating the impedance of each probe, its interaction with the electromagnetic field is changed/modulated. The change/modulation of the interaction may then be detected by an antenna, referred to as the collector antenna, at some distances from the probe. The detected modulated signal at the collector antenna may be proportional to the field at the probe's location, which may be referred to as the Modulated Scattering Technique (MST). MST-based MWI systems may provide several advantages such as, e.g., accurate near-field measurement, robust calibration, inexpensive experimental implementation, collecting various field polarizations (see, e.g., M. Ostadrahimi, A. Zakaria, J. LoVetri, and L. Shafai, "A near-field dual polarized TE-TM microwave imaging system," Microwave Theory and Techniques, IEEE Transactions on, vol. 61, no. 3, pp. 1376-1384, 2013), and an increased amount of non-redundant data (see, e.g., M. Ostadrahimi, P Mojabi, S. Noghanian, J. LoVetri, and L Shafai, "A multiprobe-per-collector modulated scatterer technique for microwave tomography," Antennas and Wireless Propagation Letters, IEEE, vol. 10, pp. 1445-1448, 2011).

SUMMARY

The exemplary systems, apparatus, and methods described herein may include antenna assemblies that are configurable so as to not perturb (e.g., non-responsive, be non-reactive to, be relatively transparent to, etc.) electromagnetic energy within a measurement domain when the antenna assemblies are not in used to image the measurement chamber. The exemplary systems, apparatus, and methods described herein may include antenna assemblies that are configurable to be used within a grain bin to image grain located within the grain bin to, e.g., detect spoiled grain, detect the grain level within the bin, etc.

One exemplary method of imaging an object using microwave tomography includes providing a plurality of antenna assemblies positionable about an object (e.g., positioned in three dimensions with respect to the object). Each antenna assembly of the plurality of antenna assemblies may include at least one reconfigurable antenna, and the at least one reconfigurable antenna of the plurality of antenna assemblies may be configurable in at least a transmit state, a receive state, and a passive state. The at least one reconfigurable antenna of the plurality of antenna assemblies may be configured to deliver electromagnetic energy to irradiate the object when in the transmit state resulting in scattered electromagnetic energy, configured to sample scattered electromagnetic energy when in the receive state, and configured to not perturb electromagnetic energy when in the passive state. The exemplary method may further include delivering electromagnetic energy using at least one antenna assembly of the plurality of antenna assemblies to irradiate the object resulting in scattered electromagnetic energy. Further, one or more of the at least one reconfigurable antenna of the at least one antenna assembly delivering electromagnetic energy may be configured in the transmit state to deliver the electromagnetic energy. The exemplary method may further include sampling the scattered electromagnetic energy using at least one antenna assembly of the plurality of antenna assemblies. Further, one or more of the at least one reconfigurable antenna of the at least one antenna assembly sampling the scattered electromagnetic energy may be configured in the receive state to sample the scattered electromagnetic energy. The exemplary method may further include configuring one or more remaining reconfigurable antennas of the plurality of antenna assemblies that are not configured in the transmit state or the receive state into the passive state and reconstructing an image (e.g., a quantitative image) of the object based on the sampled scattered electromagnetic energy.

One exemplary system for use in imaging an object using microwave tomography may include a plurality of antenna assemblies positionable about an object (e.g., positioned in three dimensions with respect to the object). Each antenna assembly of the plurality of antenna assemblies may include at least one reconfigurable antenna configurable in at least a transmit state, a receive state, and a passive state. The at least one reconfigurable antenna of the plurality of antenna assemblies may be configured to deliver electromagnetic energy to irradiate the object when in the transmit state resulting in scattered electromagnetic energy, configured to sample scattered electromagnetic energy when in the receive state, and configured to not perturb electromagnetic energy when in the passive state. The exemplary system may further include a processor coupled to the plurality of antenna assemblies and configured to deliver electromagnetic energy using at least antenna assembly of the plurality of antenna assemblies to irradiate the object resulting in scattered electromagnetic energy. Further, one or more of the at least one reconfigurable antenna of the at least one antenna assembly delivering electromagnetic energy may be configured in the transmit state to deliver the electromagnetic energy. The processor may be further configured to sample the scattered electromagnetic energy using at least one antenna assembly of the plurality of antenna assemblies. Further, one or more of the at least one reconfigurable antenna of the at least one antenna assembly sampling the scattered electromagnetic energy may be configured in the receive state to sample the scattered electromagnetic energy. The processor may be further configured to configure one or more remaining reconfigurable antennas of the plurality of antennas assemblies that are not configured in the transmit state or the receive state into the passive state and reconstruct an image (e.g., a quantitative image) of the object based on the sampled scattered electromagnetic energy.

In one or more embodiments, the method may further include providing or the system further includes boundary condition apparatus configured to present a boundary condition relative to the plurality of antenna assemblies and the object. Further, the boundary condition presented by the boundary condition may define a measurement domain, and the at least one antenna of the plurality of antenna assemblies may extend into the measurement domain. Still further, the boundary condition apparatus may include a conductive enclosure. Yet still further, the object may be grain, and the conductive enclosure may be configured to store grain. And still further, the conductive enclosure may be configured to contain a low-loss fluid.

In one or more embodiments, the at least one reconfigurable antenna of the plurality of antenna assemblies may include a first reconfigurable antenna extending along a first axis and configured to deliver or sample electromagnetic energy of at least a first polarity and a second reconfigurable antenna extending along a second axis and configured to deliver or sample electromagnetic energy of at least a second polarity. The first axis may be orthogonal to the second axis and the first polarity may be different than the second polarity. Further the at least one reconfigurable antenna of the plurality of antenna assemblies may include a third reconfigurable antenna extending along a third axis and configured to deliver or sample electromagnetic energy of at least a third polarity. The first axis may be orthogonal to the third axis and the second axis is orthogonal to the third axis, and each of the first and second polarity may be different than the third polarity.

In one or more embodiments, the at least one reconfigurable antenna of the plurality of antenna assemblies may include a plurality of conductive segments and a plurality of switchable segments coupling the conductive segments. The switchable segments may be configurable between a conducting configuration and a non-conducting configuration. The plurality of conductive segments may be electrically coupled via the switchable segments when the switchable segments are configured in the conducting configuration and maybe electrically isolated from one another when the switchable segments are configured in the non-conducting configuration. Further, the switchable segments may be configured in the conducting configuration when the antenna is configured into each of the transmit state and receive state, and the switchable segments may be configured in the non-conducting configuration when the antenna is configured in the passive state.

In one or more embodiments, each antenna assembly antennas of the plurality of antenna assemblies may include at least one ground plane, and each antenna of the at least one antenna may be mounted to a different ground plane of the at least one ground plane.

In one or more embodiments, configuring one or more remaining reconfigurable antennas of the plurality of antennas assemblies that are not configured in the transmit state or the receive state into the passive state may include configuring all of the remaining reconfigurable antennas of the plurality of antennas assemblies that are not configured in the transmit state or the receive state into the passive state.

In one or more embodiments, the at least one reconfigurable antenna of the plurality of antenna assemblies is further configurable in a probe state. Further, the at least one reconfigurable antenna of the plurality of antenna assemblies may be configured to interact with the electromagnetic energy when in the probe state. The method may further include or the processor may be further configured to execute interacting with the scattered electromagnetic energy using at least one antenna assembly of the plurality of antenna assemblies. Further, one or more of the at least one reconfigurable antenna of the at least one antenna assembly interacting with the scattered electromagnetic energy may be configured in the probe state to interact with the scattered electromagnetic energy. Still further, interacting with the scattered electromagnetic energy using at least one antenna assembly of the plurality of antenna assemblies may further include individually configuring each of the at least one reconfigurable antenna of the plurality of antenna assemblies into the probe state that is not configured in the transmit state or the receive state until every antenna of the at least one reconfigurable antenna of the plurality of antenna assemblies has been individually configured into the probe state.

In one or more embodiments, delivering electromagnetic energy using at least one antenna assembly of the plurality of antenna assemblies to irradiate the object resulting in scattered electromagnetic energy may include individually delivering electromagnetic energy with each of the at least one reconfigurable antenna of the plurality of antenna assemblies until every antenna of the at least one reconfigurable antenna of the plurality of antenna assemblies has individually delivered electromagnetic energy.

In one or more embodiments, sampling the scattered electromagnetic energy using at least one antenna assembly of the plurality of antenna assemblies may include individually sampling electromagnetic energy with each antenna of the at least one reconfigurable antenna of the plurality of antenna assemblies until every antenna of the at least one reconfigurable antenna of the plurality of antenna assemblies has individually sampled the scattered electromagnetic energy.

In one or more embodiments, each antenna assembly of the plurality of antenna assemblies may be in a fixed position relative to the object. Further, each of the at least one reconfigurable antenna of the plurality of antenna assemblies may be stationary with respect to each other.

Exemplary systems, apparatus, and methods using reconfigurable multiple-polarization antennas for microwave imaging systems are described herein. The exemplary systems, apparatus, and methods can be adapted to various biomedical, clinical, and industrial imaging applications within any type of imaging domain. One exemplary microwave system using these antennas may include an array of multiplexed, multipolarized transmitting/collecting reconfigurable antennas printed on a printed circuit boards (PCB). The exemplary antennas may be positioned around the circumference of an imaging system in multiple layers (e.g., stacked vertical layers). Each antenna may include a radiating element, may have multiple polarizations, and may be divided in several sections that are connected through a switch (such as, e.g., P-I-N diodes, micromechanical system (MEMS) switches, etc.). The switches can be biased in three different states such as, e.g., open, short, or modulated, and may enable the antenna to illuminate an object-of-interest by microwave energy or to measure field scattered by the object-of-interest, based on different exemplary techniques and processes. Further, these antennas can be used for either a single polarization data collection when positioned vertically, horizontally, slant, or perpendicular to the measurement chamber, or the antennas can have any combinations of these orientations (e.g., even all of the aforementioned polarizations). Different orientations can collect various field polarizations such as, e.g., transverse electric (TE), transverse magnetic (TM), normal field, or a combination of different polarizations, without the need for mechanical movement.

To illuminate the object with all possible polarizations of the electromagnetic field, arbitrary orientations of the antennas can be configured. Further, the data collected using the reconfigurable antennas may then be calibrated based on the orientation/polarization of the antennas. The calibrated data can be used to reconstruct the dielectric profile of various objects using exemplary three-dimensional inversion algorithms. Still further, a highly-sensitive, coherent receiver may also be used, which may allow one to decrease the power used for illumination of the object-of-interest.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 5 is a flow diagram for an exemplary imaging method, e.g., for use with the imaging setup, system, antennas, and antenna assemblies of FIGS. 1-4.

FIG. 7 depicts an exemplary antenna assembly configuration.

FIG. 8 are exemplary images of an electromagnetic field distribution in a measurement chamber with only the transmitting antenna located in the measurement chamber.

FIG. 9 are exemplary images of an electromagnetic field distribution in a measurement chamber with the transmitting antenna and a plurality of additional antennas located in the measurement chamber.

DETAILED DESCRIPTION OF EXEMPLARY EMBODIMENTS

Exemplary methods, apparatus, and systems shall be described with reference to FIGS. 1-28. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 1:
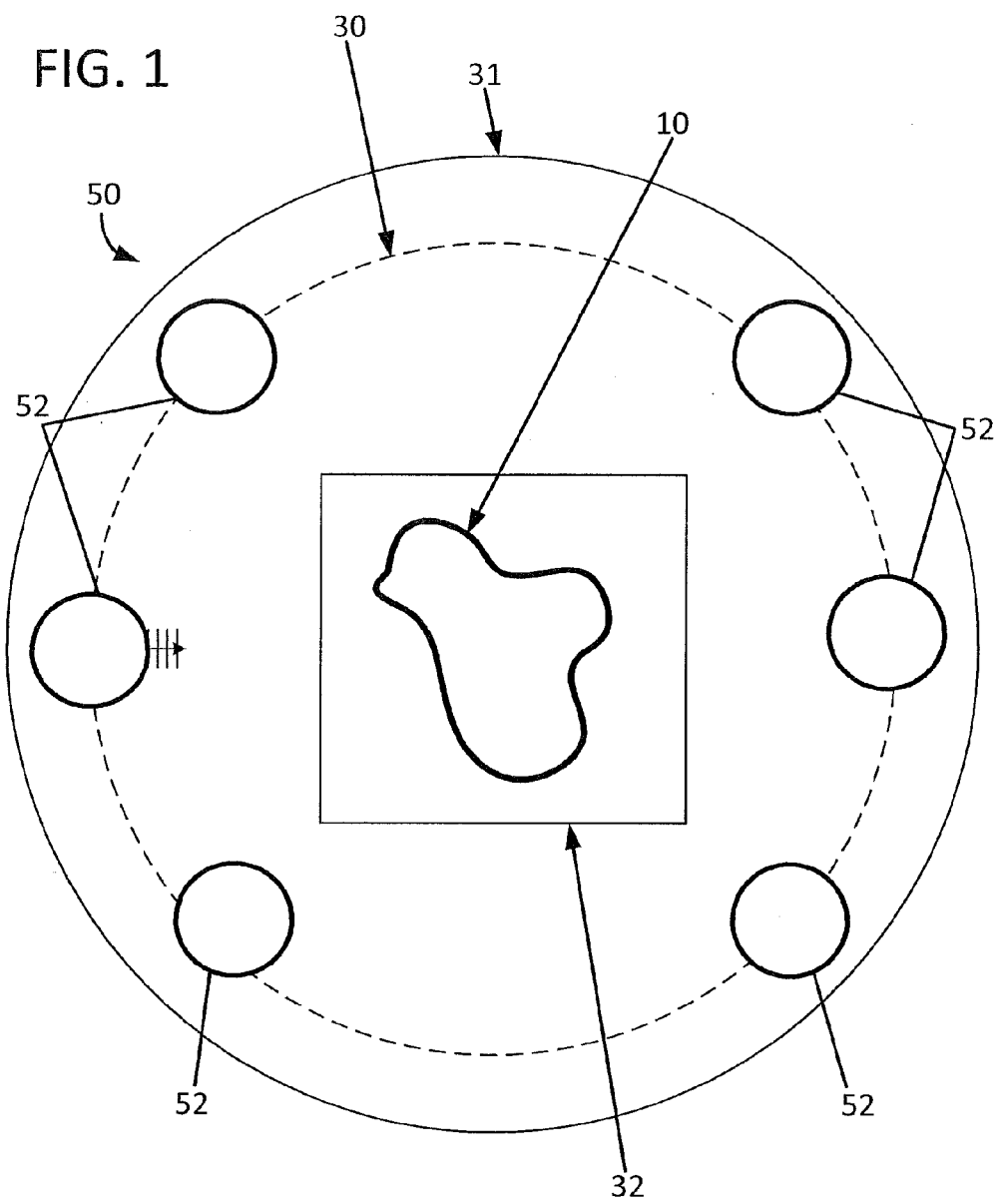
FIG. 1 is a plan view of an exemplary imaging setup.

An exemplary imaging setup 50, or configuration, is depicted in FIG. 1. The imaging setup 50 includes a plurality of antenna assemblies 52 diagrammatically represented by circles positioned about an object of interest (OI) 10. Although not depicted, each antenna assembly 52 may include one or more antennas or at least one of antenna (e.g., a plurality of antennas) as described further herein. The plurality of antenna assemblies 52 may be positioned about the object of interest (OI) 10. In one or more embodiments, the plurality of antenna assemblies 52 may be positioned completely around the object (e.g., around an axis in a plane, in multiple planes, etc.). In one or more embodiments, the plurality of antenna assemblies 52 may be positioned partially around the object of interest 10 such as one quarter around the OI 10, halfway around the OI 10, three quarters around the OI 10, etc.

As shown in FIG. 1, the exemplary imaging setup 50 includes six antenna assemblies 52 spaced about the object of interest 10 defining a measurement domain 30. The measurement domain 30 may be defined as the area within an electromagnetic scattered field created by the imaging setup 50 within which data may be gathered using the imaging setup 50. Further, the imaging setup 50 may be configured to image an imaging domain 32 containing the object 10 located within the measurement domain 30. The imaging domain 32 may be a subset, or portion, of the measurement domain 30.

The exemplary imaging setups 50 described herein may include any number of antenna assemblies 52. For example, the exemplary imaging setups 50 may include 2 or more antenna assemblies, 3 or more antenna assemblies, 5 or more antenna assemblies, 6 or more antenna assemblies, 7 or more antenna assemblies, 10 or more antenna assemblies, 12 or more antenna assemblies, 16 or more antenna assemblies, 24 or more antenna assemblies, etc. Further, the exemplary imaging setups 50 may include 50 or less antenna assemblies, 40 or less antenna assemblies, 36 or less antenna assemblies, 30 or less antenna assemblies, 24 or less antenna assemblies, 18 or less antenna assemblies, 16 or less antenna assemblies, 8 or less antenna assemblies, etc. Further, although as shown in the diagrammatic view of the system 50 the antenna assemblies 52 appear to lie in the same plane, it is to be understood that the exemplary antenna systems, apparatus, and methods described herein may include antenna assemblies positioned "three-dimensionally" with respect to each other. For example, not all of the antenna assemblies 52 may lie in the same plane. In a vertically-oriented chamber where the chamber extends along a vertical axis, the antenna assemblies 52 may be positioned about the perimeter of the chamber at different vertical levels or the same vertical level. In at least one embodiment, a portion of antenna assemblies 52 may be positioned at a selected vertical level while another portion of antenna assemblies 52 may be positioned at a different selected vertical level.

The antenna assemblies 52 of the imaging setup 50 may be located about the object 10 in any spacing and/or distance from the object 10 so as to be able to provide scattering data (e.g., measurements with respect to a scattered electromagnetic field resulting from delivering electromagnetic energy to the object of interest) useful for the reconstruction of an image (e.g., quantitative image) of the object 10. The antenna assemblies 52 may be in a fixed position relative to each other and/or to the object 10 during imaging such that the position of the antenna assemblies does not change during imaging. For example, the antenna assemblies 52 may be attached to a structure such as a measurement chamber 31 as depicted within which the object 10 may be located. In at least one embodiment, the antenna assemblies 52 may be positioned around a perimeter of the object.

Further, the antenna assemblies 52 may extend from or at least be located within the measurement chamber 31. For example, the measurement chamber 31 may define an inner wall facing the measurement domain 30 and imaging domain 32, and at least the antennas of the antenna assemblies 52 may be coupled to the inner wall of the measurement chamber 31 and extend from the inner wall radially towards the center of the measurement chamber 31.

Additionally, the measurement chamber 31 may be a chamber of any shape defining at least a portion of the measurement domain 30. Although as shown the measurement domain 30 is a subset (e.g., smaller than and completely contained within) the measurement chamber 31, it is to be understood that the measurement chamber 31 may define the entire measurement domain 30 (e.g., all area within the measurement chamber 31 may be the measurement domain 30).

In one or more embodiments, the measurement chamber 31 may be a grain bin, or silo, and the OI 10 may be grain located within the grain bin. Further, the interior of the grain bin may be the measurement domain 30 and the imaging domain 32 may also be in the interior (or part of the interior) of the grain bin. Further, the antenna assemblies 52 may be located within the grain bin and at least a portion measurement domain 30. For example, the antenna assemblies 52 may partially extend from the interior walls of the grain bin into at least part of the measurement domain 30.

Further, in one or more embodiments, the antenna assemblies 52 may be attached to the object 10 itself. In at least one embodiment, the antenna assemblies 52 may be attached to a belt-like apparatus that may be wrapped around the object 10.

The positions, or locations, of the antenna assemblies 52 with respect to each other may be useful to provide scattering data for reconstruction of an image of the object 10. When the antenna assemblies 52 are attached to a structure such as a measurement chamber 31, the positions of the antenna assemblies 52 are already known (e.g., due to being fixed to the structure). When the antenna assemblies 52 are not attached to a structure, and instead attached to the object 10 itself or not-fixedly arranged prior to imaging, a calibration procedure may be executed to determine the positions/locations of the antenna assemblies prior to imaging as described further herein.

As shown in FIG. 1, the antenna assemblies 52 are located equidistantly from the center of the imaging domain 32 and spaced equidistantly from each other. In other embodiments, the antenna assemblies 52 may not be equidistantly from the center of the imaging domain 32 and/or spaced equidistantly from each other.

Figure 2:
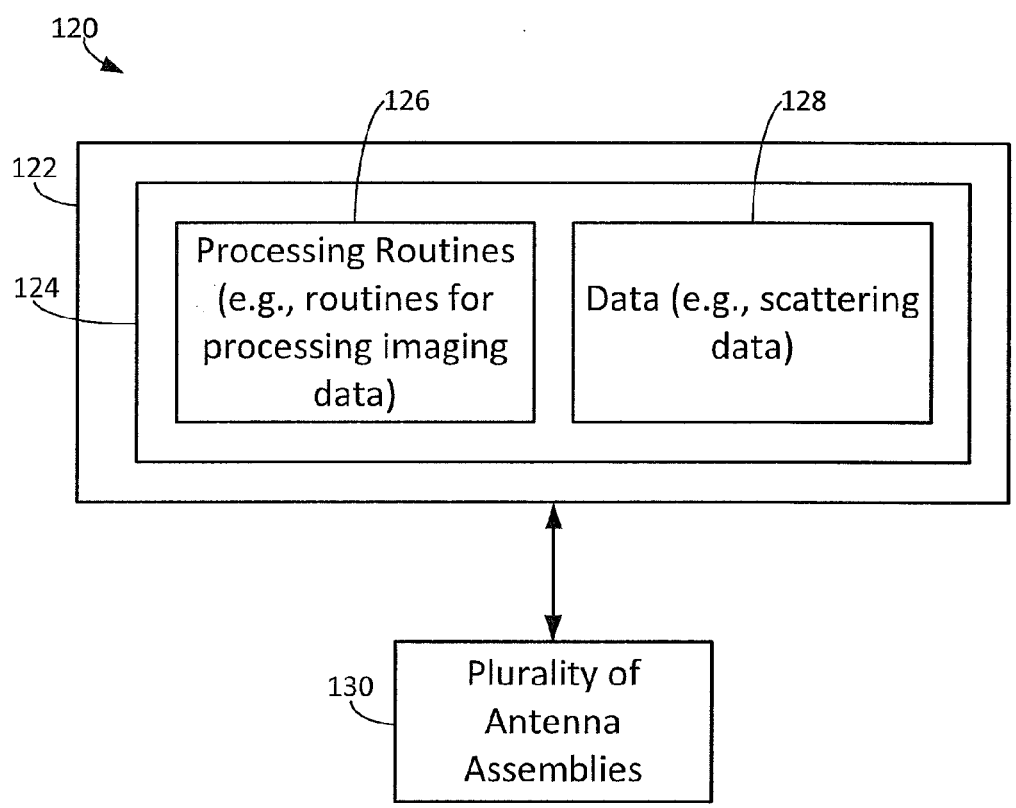
FIG. 2 is a block diagram of an exemplary imaging system, e.g., for use with the imaging setup of FIG. 1.

An exemplary imaging system 120 (e.g., a MWI imaging system), e.g., for use with the imaging setup, apparatus, methods, and results of FIGS. 1-28 is depicted in FIG. 2. The system 120 may include a processor, or processing apparatus, 122 and a plurality of antenna assemblies 130 (e.g., the antenna assemblies 52 of imaging setup 50). The processor 122 may be operably coupled to the plurality of antenna assemblies 130 to facilitate imaging of an object of interest using the antenna assemblies 130. Generally, the processor 122 may control the image data acquisition using the plurality of antenna assemblies 130 and may perform the image reconstruction. More specifically, the processor 122 may be configured to control and/or initiate the functionality of the plurality of antenna assemblies 130 for use in imaging an object. For example, the processor 122 may configure the reconfigurable antennas, described further herein, of the antenna assemblies 52 into various states such as transmit, receive, and passive states. Then, for example, the processor 122 may deliver electromagnetic energy with a reconfigurable antenna of an antenna assembly 52 configured in the transmit state to the object of interest/imaging domain and measure the scattered electromagnetic field with a reconfigurable antenna of an antenna assembly 52 configured in the receive state to provide data for image reconstruction.

Further, the processor 122 includes data storage 124. Data storage 124 allows for access to processing programs or routines 126 and one or more other types of data 128 that may be employed to carry out the exemplary imaging methods. For example, processing programs or routines 126 may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein.

Data 128 may include, for example, sampled electromagnetic energy (e.g., sampled or collected using the plurality of antenna assemblies 130 in the absence of any object, thereby collecting the incident field, or using a calibration object) including the amplitude and/or phase, data representative of measurements (e.g., electromagnetic scattering data), information on the location and polarity of the collected data, results from one or more processing programs or routines employed according to the disclosure herein (e.g., reconstructed images of an object of interest), or any other data that may be necessary for carrying out the one or more processes or methods described herein.

In one or more embodiments, the system 120 may be implemented using one or more computer programs executed on programmable computers, such as computers that include, for example, processing capabilities (e.g., microcontrollers, programmable logic devices, etc.), data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 120 may be implemented using a computer readable storage medium, configured with a computer program, where the storage medium so configured causes the computer to operate in a specific and predefined manner to perform functions described herein.

Likewise, the imaging system 120 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processor 122 may be, for example, any fixed or mobile computer system (e.g., a personal computer or mini computer). The exact configuration of the computing apparatus is not limiting and essentially any device capable of providing suitable computing capabilities and control capabilities (e.g., control the imaging set up configuration and acquire data, such as electromagnetic scattering data) may be used. Further, various peripheral devices, such as a computer display, mouse, keyboard, memory, printer, scanner, etc. are contemplated to be used in combination with the processor 122.

Further, in one or more embodiments, the output (e.g., an image, image data, incident field data, scattered field data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus 124 described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct the images described herein (e.g., from sampled electromagnetic scattering data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

The methods described in this disclosure, including those attributed to the systems, or various constituent components, may be implemented, at least in part, in hardware, software, firmware, or any combination thereof. For example, various aspects of the techniques may be implemented by processor, or processing apparatus, 122 may use one or more processors, including one or more microprocessors, DSPs, ASICs, FPGAs, CPLDs, microcontrollers, or any other equivalent integrated or discrete logic circuitry, as well as any combinations of such components, image processing devices, or other devices. The term "processing apparatus," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Imaging systems, apparatus, and methods may be described U.S. Pat. App. Pub. No. 2011/0227586 A1 entitled "Microwave Tomography Systems and Methods" and filed Mar. 18, 2011, U.S. Pat. App. Pub. No. 2011/0227586 A1 entitled "Microwave Tomography Systems and Methods" and filed Mar. 18, 2011, PCT Pat. App. Pub. No. WO 2013/005134 entitled "Imaging Using Probes" and published on Jan. 10, 2013, U.S. Provisional Pat. App. Ser. No. 61/921,808 entitled "Imaging Using Gated Elements" and filed on Dec. 30, 2013, and PCT Pat. App. Ser. No. PCT/IB2014/067390 entitled "Imaging Using Gated Elements and filed on Dec. 29, 2014, each of which is incorporated by reference herein in their entireties.

Figure 3:
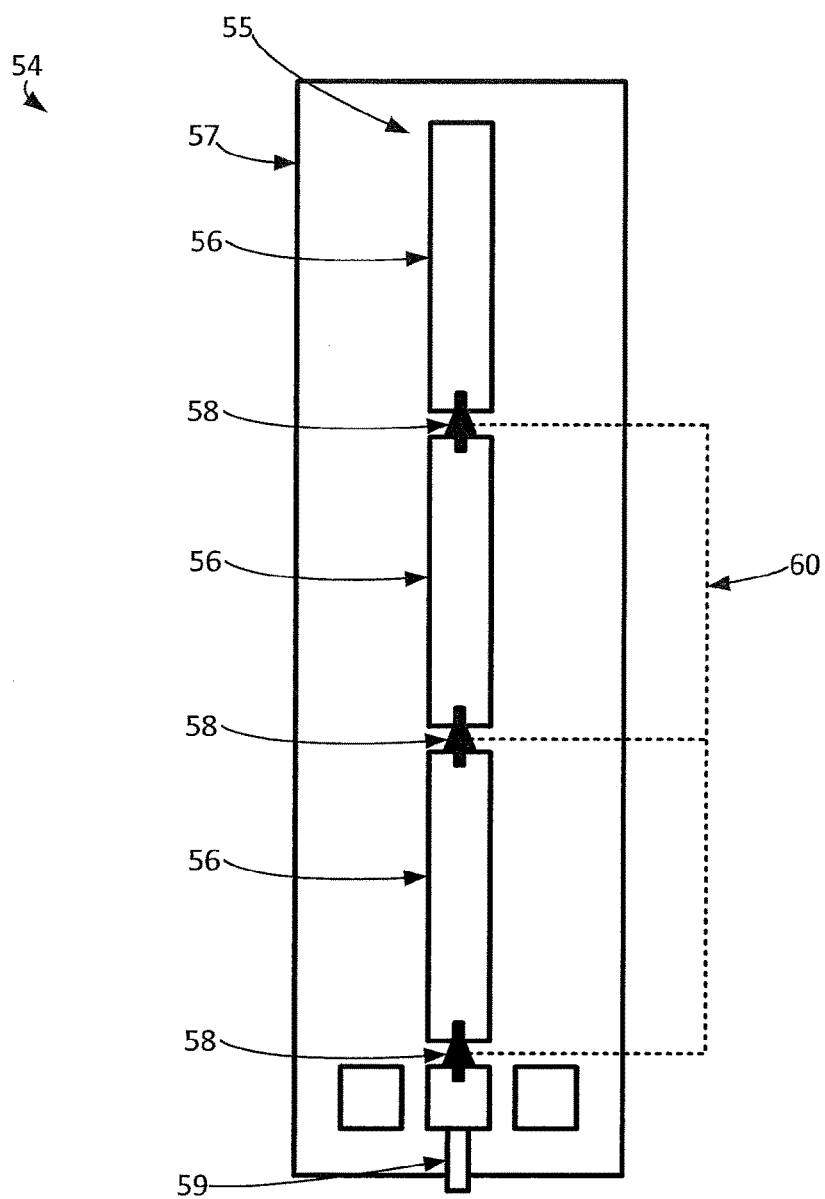
FIG. 3 is a diagrammatic depiction of an exemplary reconfigurable antenna, e.g., for use with the imaging setup of FIG. 1.

A diagrammatic representation of an exemplary reconfigurable antenna 54 for use in an antenna assembly is 52 is depicted in FIG. 3. The reconfigurable antenna 54 may be described as being reconfigurable because the reconfigurable antenna 54 may be configurable in a plurality of states for use in the exemplary imaging systems, apparatus, and methods described herein. For example, the antenna 54 may configured in a transmit state, a receive state, a probe state, and a passive state.

The exemplary reconfigurable antenna 54 may include may include conductive segments 56, switchable segments 58, a ground plane 57, and a port 59. The conductive segments 56 may include one or more conductive materials such as, e.g., copper, aluminum, silver, gold, brass, etc. In at least one embodiment, the conductive segments 56 include copper. The reconfigurable antenna 54 may configured in a transmit state, a receive state, a probe state, and a passive state through the use of the switchable segments 58 (e.g., switches, embedded P-I-N diodes, etc.). The switchable segments 58 may be P-I-N diodes electrically coupling the conductive segments 56 in serial. Although, as shown, the exemplary antenna 54 includes three conductive segments 56 and three switchable segments 58, exemplary antennas and antenna assemblies may include any number of conductive segments 56 and/or switchable segments 58 so as to provide the transmit, receive, passive, and probe states or configurations.

The switchable segments 58 may be reverse biased ("off") to electrically un-couple the conductive segments 56 from each other to place the reconfigurable antenna 54 in a passive state. When in the passive state, the reconfigurable antenna 54 may not perturb, not disturb, or not react with electromagnetic energy in the imaging system. In other words, when the reconfigurable antenna 54 is configured in the passive state, the reconfigurable antenna 54 may be "invisible" or "transparent" to electromagnetic energy. Further, the switchable segments 58 may be forward biased ("on") so as to "short" the spacings (e.g., conductive couplings) between the conductive segments 56 to electrically couple the conductive segments 56 to place the reconfigurable antenna 54 in a transmit or receive state. When using a modulated scattering process or technique, the switchable segments 58 may be modulated with a modulation signal (e.g., square wave signal) to electrically short, or couple, the conductive segments 56 in accordance with the modulation signal to place the reconfigurable antenna 54 in a probe, or scattering, state. Each switchable segment 58 may be coupled to a bias wire 60 (symbolically depicted by dotted lines) configured to apply a signal to the switchable segments 58 to place the switchable segments 58 in a forward bias, reverse, bias, or modulated state as described further herein.

Although not shown, the bias wires 60 may be placed on top of the ground plane 57, e.g., so as to not interfere, or perturb, the imaging process. More specifically, the ground plane 57 may shield the bias wires 60 from interaction with the electromagnetic fields in the measurement domain. The port 59 (e.g., radio frequency port) may be configured to be coupled to the remainder of the exemplary system 120 that samples the scattered electromagnetic field and provides the electromagnetic energy for transmission into the measurement domain. One or more (e.g., all) of the components or parts of the antenna 54 such as the conductive segments 56, switchable segments 58, the ground plane 57, and the port 59 may be part of, or attached to, a printed circuit board (PCB). For example, the ground plane 57 may be a metallic surface of a PCB, the conductive segments 56 may be metallic traces on the PCB, the switchable segments 58 may be soldered to the PCB between the conductive segments 56.

Figure 4:
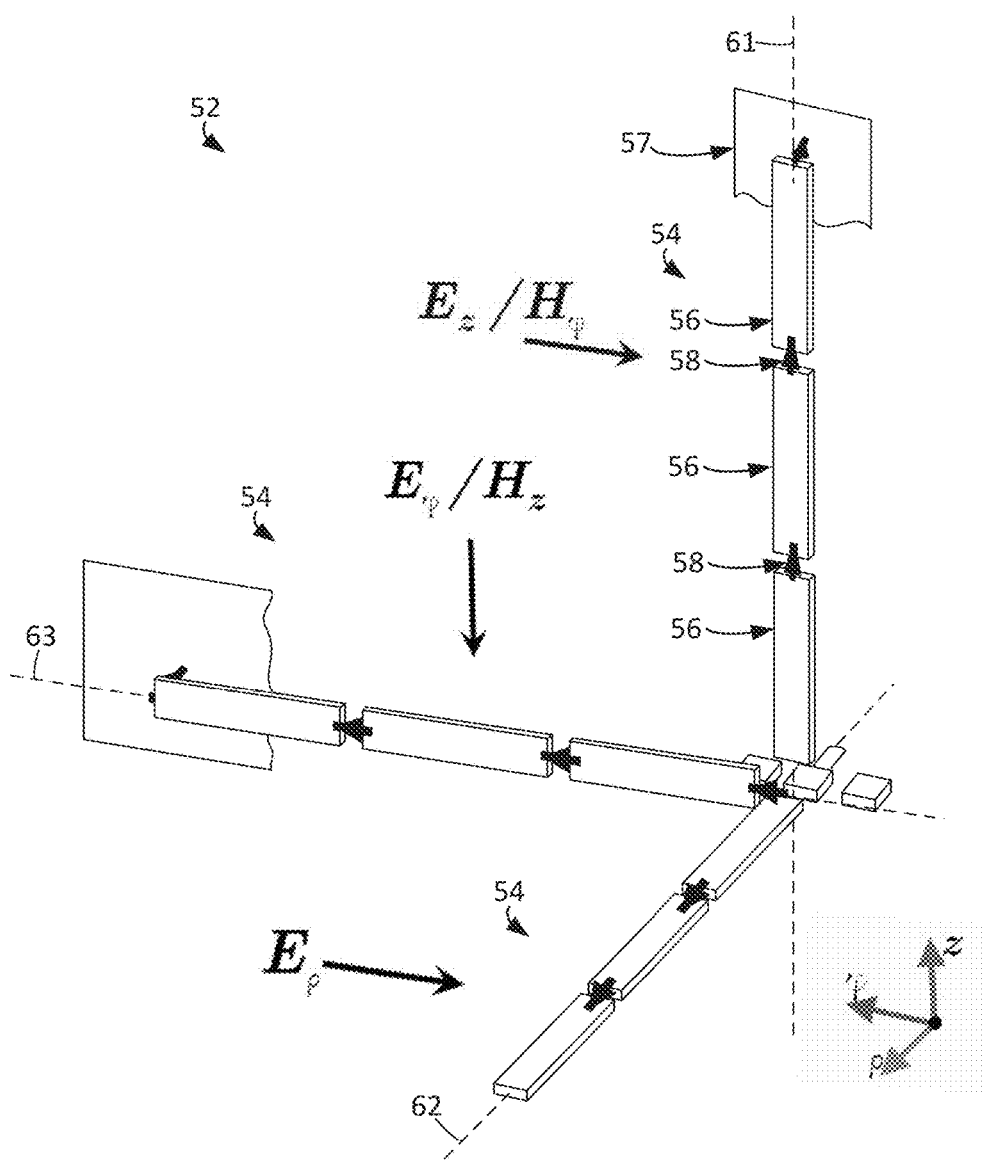
FIG. 4 is a diagrammatic depiction of an exemplary reconfigurable antenna assembly, e.g., for use with the imaging setup of FIG. 1.

As described herein, each antenna assembly 52 may include one or more reconfigurable antennas 54. An exemplary antenna assembly 52 including three antennas is depicted in FIG. 4. As shown, the antenna assembly 52 includes a first antenna 52 extending along a first axis 61, a second antenna 52 extending along a second axis 62, and a third antenna 52 extending along a third axis 63. The first axis 61 is perpendicular, or orthogonal, to the second and third axes 62, 63, the second axis 62 is perpendicular, or orthogonal, to the first and third axes 61, 63, and the third axis 63 is perpendicular, or orthogonal, to the first and second axes 61, 62. The arrangement of the antennas 54 along such axes 61, 62, 63 allows, or configures, each of the first, second, and third antennas 54 to transmit, receive, and/or interact with (e.g., disturb, perturb, react with, scatter, etc.) electromagnetic energy of a different polarity from one another. More specifically, due to the perpendicular relationships between the antennas 54, the first antenna 54 may be configured to transmit, receive, and/or interact with electromagnetic energy of a polarity that is perpendicular, or orthogonal, to the polarities of the electromagnetic energy that the second and third antennas 54 are configured to transmit, receive, and/or interact with, the second antenna 54 may be configured to transmit, receive, and/or interact with electromagnetic energy of a polarity that is perpendicular, or orthogonal, to the polarities of the electromagnetic energy that the first and third antennas 54 are configured to transmit, receive, and/or interact with, and third antenna 54 may be configured to transmit, receive, and/or interact with electromagnetic energy of a polarity that is perpendicular, or orthogonal, to the polarities of the electromagnetic energy that the first and second antennas 54 are configured to transmit, receive, and/or interact with.

A flow chart of an exemplary imaging method 80 for imaging an object is depicted in FIG. 5. One will recognize that one or more of the blocks of functionality described herein may be carried out using one or more programs or routines, and/or any other components of the exemplary imaging systems and/or setups described herein (e.g., the imaging setup 50 of FIG. 1, the imaging system 120 of FIG. 2, etc.).

The method 80 includes providing a plurality of antenna assemblies positionable about an object 82. The antenna assemblies, as well as the remainder of the system and apparatus used in method 80, may be similar to the antenna assemblies 52, 130 and systems 50, 120 described herein with reference to FIGS. 1-4. For example, the antenna assemblies may include a plurality of antennas, each configurable in at a transmit state, receive state, and passive state. Further, each of the plurality of antennas may be configurable in a probe state if, e.g., an indirect, modulated scattering technique or an indirect, differential scattering technique is used.

The imaging method 80 may include a plurality of imaging iterations as represented by the loop arrow 81. Each iteration may provide more scattering data to be used in the image reconstruction. For each iteration, the plurality of antennas may be configured differently 84. For example, at least one reconfigurable antenna may be configured in the transmit state to deliver electromagnetic energy to irradiate the object resulting in scattered electromagnetic energy and at least another at least one reconfigurable antenna may be configured in the receive state to sample the scattered electromagnetic energy. Further, a plurality of remaining antennas that are not configured in the transmit state or the receive state may be configured into the passive state e.g., so as to not react with, not perturb, not disturb, etc. the electromagnetic energy (further, e.g., such that the passive antennas are invisible or transparent to the electromagnetic energy in this iteration). Further, if the method 80 is using an indirect imaging scheme, and thus using scattering probes, at least one reconfigurable antenna may be configured in a probe state.

Once the antenna are configured for a particular iteration, the antenna configured in the transmit state may deliver electromagnetic energy 86 (e.g., electromagnetic energy generated by a microwave source at a frequency in the range of about 0.3 GHz to about 20 GHz), the antenna configured in the receive state may sample electromagnetic energy 87, and, if the method is using an indirect imaging scheme, the antenna configured in the probe state may be modulated 88. The method 80 may then loop 81 back to the configuration process 84 to, e.g., configure the antennas in another, unique combination. The method 80 may continue looping until each antenna has delivered electromagnetic energy, and for each antenna delivering electromagnetic energy, each antenna has sampled electromagnetic energy (e.g., the resultant scattered field). Further, if the method is using an indirect imaging scheme, the method 80 may continue looping until each antenna has been configured in the probe state and modulated to be a scattering probe, and for each antenna delivering electromagnetic energy and for each antenna modulated to be a scattering probe, each antenna has sampled electromagnetic energy (e.g., the resultant scattered field).

After the method 80 has finished looped, an image representative of the object or a portion thereof may be reconstructed (e.g., using inversion) based on the sampled electromagnetic energy 90 as described further herein.

Figure 6A:
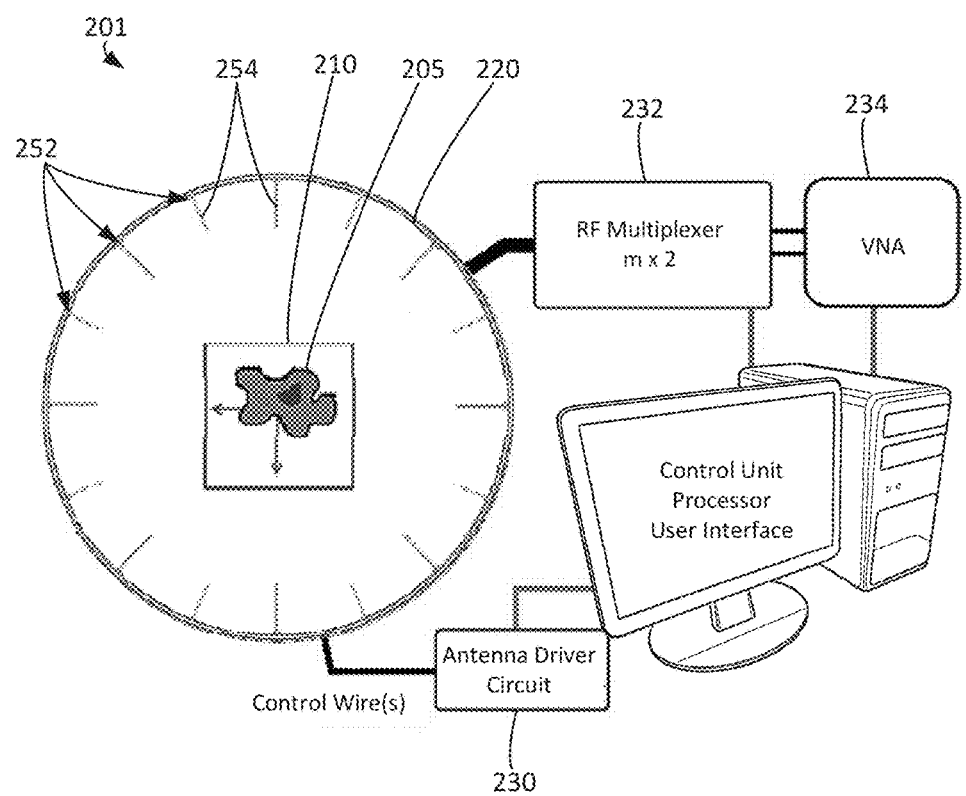
FIGS. 6A-6C depicts exemplary imaging systems.
Figure 6B:
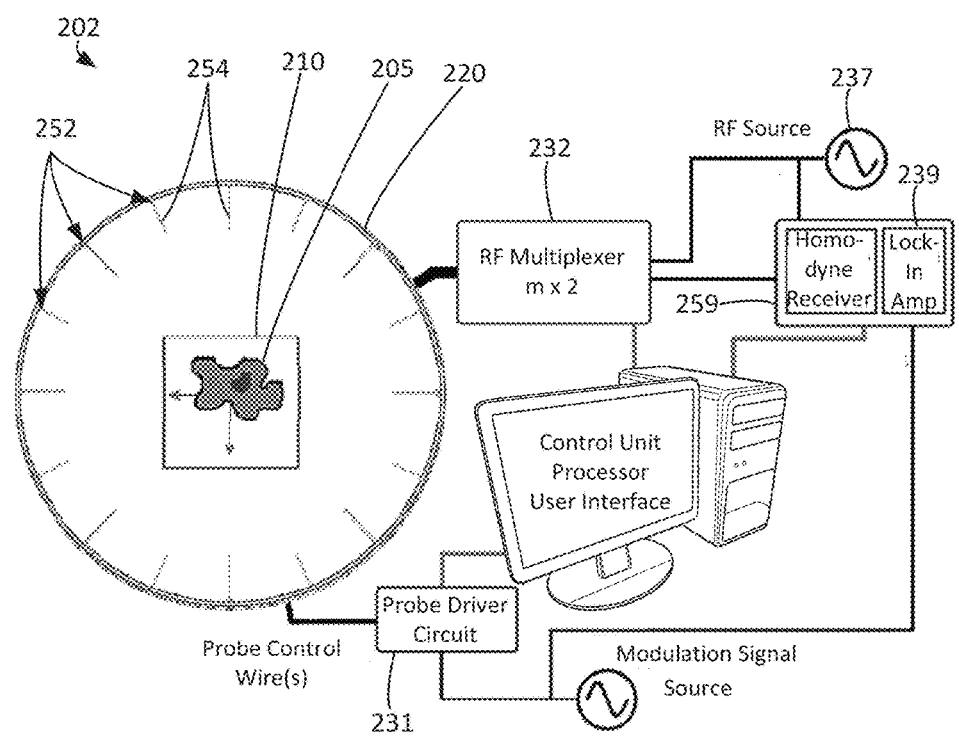
Figure 6C:
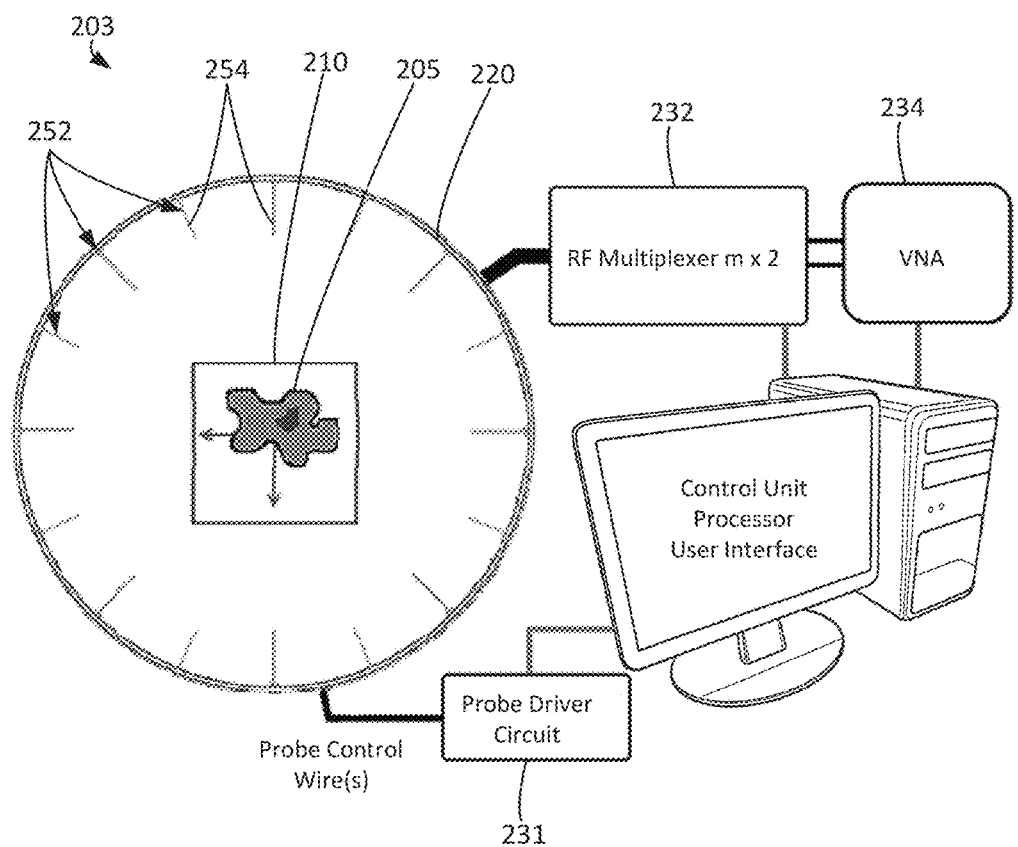
Figure 10:
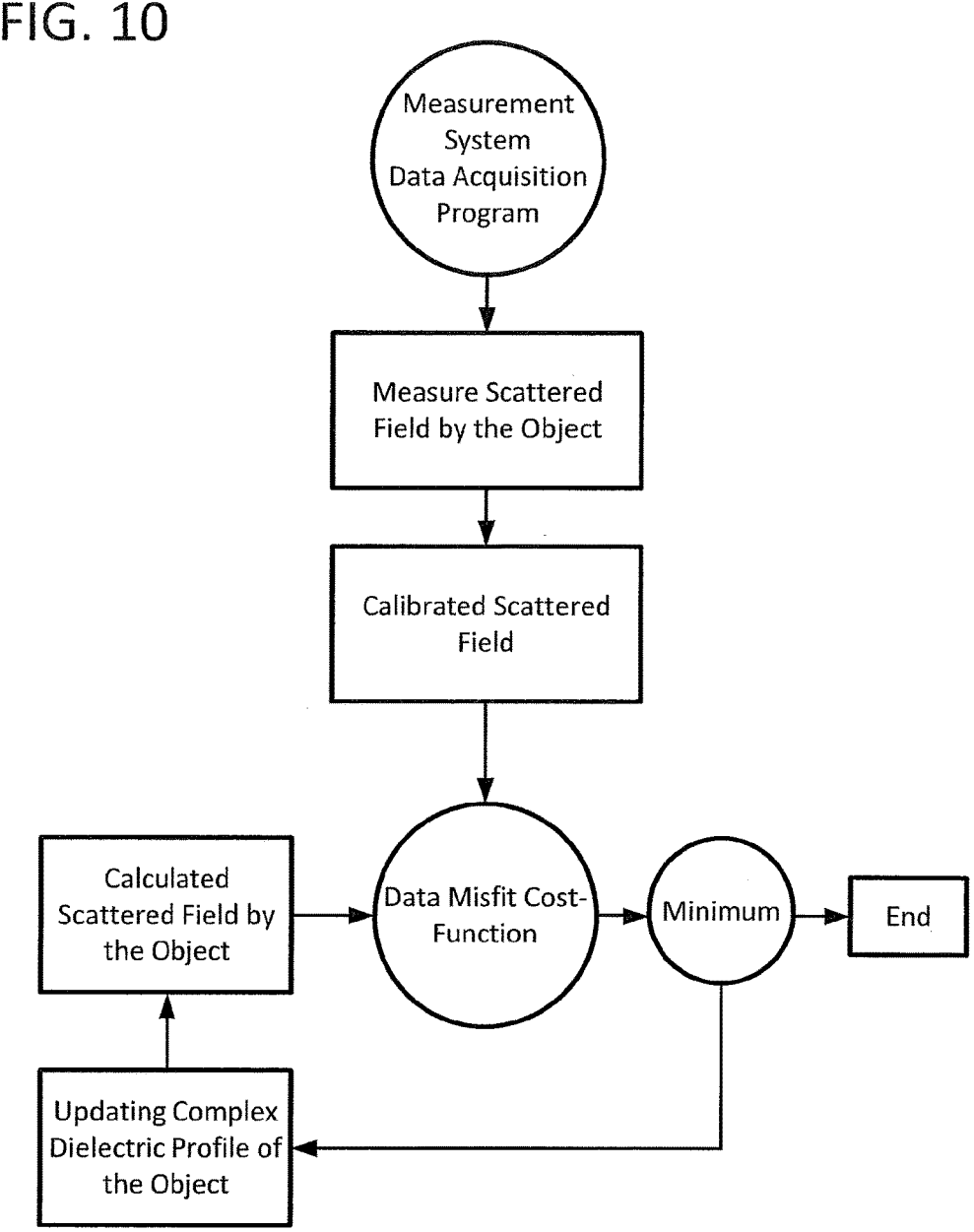
FIG. 10 is a flow diagram for an exemplary imaging method for use with the systems, apparatus, and methods described herein.

The exemplary imaging systems (e.g., microwave imaging systems) described herein may use a variety of different processes and methods. Three different exemplary imaging methods are described herein with reference to the exemplary systems depicted in FIGS. 6A-6C. For example, an exemplary direct field measurement system using a vector network analyzer (VNA) is depicted in FIG. 6A, an exemplary indirect field measurement using coherent detection is depicted in FIG. 6B, and an indirect differential $S_{12}$ measurement system using a VNA is depicted in FIG. 6C.

In the first exemplary method, the imaging system 201 may include a plurality of antenna assemblies 252, and each antenna assembly 252 may include a reconfigurable antenna 254 to directly measure the electromagnetic fields (see, e.g., C. Gilmore, A. Zakaria, P. Mojabi, M. Ostadrahimi, S. Pistorius, and J. Lo Vetri, "The University of Manitoba microwave imaging repository: a two-dimensional microwave scattering database for testing inversion and calibration algorithms," Antennas and Propagation Magazine, IEEE, vol. 53, no. 5, pp. 126-133, October 2011, which is incorporated herein by reference in its entirety). In the second exemplary method, the imaging system 202 may use the modulated scattering technique (MST) (see, e.g., M. Ostadrahimi, M. Asefi, J. LoVetri, G. Bridges, and L. Shafai, "An mst-based microwave tomography system using homodyne receiver," in Antennas and Propagation Society International Symposium, 2013. APSURSI'13. IEEE. IEEE, 2013, pp. 1-4, which is incorporated herein by reference in its entirety) to measure the scattered field by the OI 205. In the third exemplary method, the exemplary system 203 may use a differential scattering technique (DST) to indirectly measure the scattered field by the OI 205 (see, e.g., M. Ostadrahimi, P. Mojabi, S. Noghanian, L. Shafai, S. Pistorius, and J. LoVetri, "A novel microwave tomography system based on the scattering probe technique," IEEE Trans. Instrum. Meas., vol. 61, no. 2, pp. 379-390, February 2012, which is incorporated herein by reference in its entirety).

In the second approach, some of the reconfigurable antennas 254 may be used as field measurement probes. When the reconfigurable antennas 254 are utilized as field measurement probes, the reconfigurable antennas 254 may be used to infer the electromagnetic field impinging on their location. By changing/modulating the impedance of each reconfigurable antenna 254, the interaction of the reconfigurable antenna 254 with the electromagnetic field may changes or get modulated. The change/modulation of the interaction may then be detected by another reconfigurable antenna 254, referred to as the collector antenna, at some distance from the measurement probe reconfigurable antenna 254. The detected modulated signal at the collector reconfigurable antenna 254 is proportional to the field at the location of the measurement probe reconfigurable antenna 254. This exemplary technique may be described as the modulated scattering technique (MST). MST-based systems may provide, e.g., accurate near-field measurement, robust calibration, inexpensive experimental implementation (see, e.g., M. Ostadrahimi, P. Mojabi, S. Noghanian, L. Shafai, S. Pistorius, and J. LoVetri, "A novel microwave tomography system based on the scattering probe technique," IEEE Trans. Instrum. Meas., vol. 61, no. 2, pp. 379-390, February 2012, which is incorporated herein by reference in its entirety), collecting various field polarizations (see, e.g., M. Ostadrahimi, A. Zakaria, J. LoVetri, and L. Shafai, "A near-field dual polarized (TE-TM) microwave imaging system," IEEE Trans. Microw. Theory Techn., vol. 61, no. 3, pp. 1376-1384, March 2013, which is incorporated herein by reference in its entirety), and increasing the amount of non-redundant data from the system (see, e.g., M. Ostadrahimi, P. Mojabi, S. Noghanian, J. LoVetri, and L. Shafai, "A multiprobe-percollector modulated scatterer technique for microwave tomography," Antennas and Wireless Propagation Letters, IEEE, vol. 10, pp. 1445-1448, 2011, which is incorporated by reference herein in its entirety).

The modulation of the modulation probe reconfigurable antenna 254 may be implemented by switching the impedance of the reconfigurable antenna 254 in two cases: in the first case, the switchable segments (e.g., diodes) are forward biased; and in second case, the switchable segments (e.g., diodes) are reversed biased. In each case, the perturbation of the modulation probe reconfigurable antenna 254 of the electromagnetic field may be detected by a collector antenna using a vector network analyzer (VNA) (see, e.g., M. Ostadrahimi, P. Mojabi, S. Noghanian, L. Shafai, S. Pistorius, and J. LoVetri, "A novel microwave tomography system based on the scattering probe technique," IEEE Trans. Instrum. Meas., vol. 61, no. 2, pp. 379-390, February 2012, and M. Ostadrahimi, A. Zakaria, J. LoVetri, and L. Shafai, "A near-field dual polarized (TE-TM) microwave imaging system," IEEE Trans. Microw. Theory Techn., vol. 61, no. 3, pp. 1376-1384, March 2013, each of which is incorporated herein by reference in their entireties) or a custom-designed coherent receiver (see, e.g., M. Ostadrahimi, M. Asefi, J. LoVetri, G. Bridges, and L. Shafai, "An mst-based microwave tomography system using homodyne receiver," in Antennas and Propagation Society International Symposium, 2013. APSURSI'13. IEEE. IEEE, 2013, pp. 1-4, which is incorporated herein by reference in its entirety). Further, the exemplary system may change to use a coherent detector 259 instead of a VNA 234.

In the following examples, exemplary systems, methods, and apparatus may be used implement a 3-D vectorial MWI system that may have a high degree of accuracy and consistency. The exemplary systems, methods, and apparatus may use printed-circuit-board (PCB) technology, and include reconfigurable antennas that are electronically controlled to operate either as (1) a transmitter, a receiver, or a differential scattering technique (DST) or MST probe or (2) a passive, non-reactive element (e.g., non-reactive, non-perturbing, non-disturbing to electromagnetic energy). Since the reconfigurable antennas may be manufactured on PCBs, the antennas may be manufactured consistently and accurately. Furthermore, the reconfigurable antennas may include, or be built to be mounted on, a ground plane, and the biasing wires may be placed on top of the ground plane and do not interfere with the MWI operation (e.g., the bias wires may be shielded by the ground plane).

The exemplary reconfigurable antennas (RAs) may be described as providing minimum field perturbation at the desired frequency of operation, which may make the reconfigurable antennas desirable in MWI systems that are bounded by perfect electric conductor (PEC) enclosures such as grain bins and other systems may require minimum interference from the existing signals in their surrounding such as biomedical applications.

As described herein, the exemplary systems 201, 202, 203 may include a plurality of antenna assemblies 252. In at least this embodiment, the antenna assembly 252 may be a printed reconfigurable monopole antenna 254 on a printed circuit board distributed in multiple layers inside a chamber (e.g., multiple vertical layers). Each reconfigurable monopole antenna may be printed on both sides of a multi-layered PCB and may include of a set of switchable elements (e.g., PIN or P-I-N diodes) located at certain spacings between conductive elements. The monopoles may also include capacitors and resistors (or inductors), e.g., that are used for coupling/decoupling the radio frequency (RF) and direct current (DC) signals on each reconfigurable antenna 254. The switchable elements may be used to control the operation of the reconfigurable antennas 254 in different modes, and may be controlled through a driver circuit, which may bias or un-bias the reconfigurable antennas 254. If a reconfigurable antenna 254 is biased, the switchable elements of the reconfigurable antenna 254 are "on" or "shorted." If a reconfigurable antenna 254 is unbiased, the switchable elements of the reconfigurable antenna 254 are "off" or "opened."

The driver circuit 230, 231 may be referred to as the probe-driver-circuit (PDC). Further, the antennas 254 may be connected to an M-to-2 RF multiplexer/switch 232 that is followed by a VNA 234. To increase the sensitivity of the exemplary systems 201, 202, 203, indirect method may be used where the scattering probes can be modulated and the VNA 234 may be replaced by a signal generator (e.g., a RF source) 237 and a sensitive coherent receiver 259. The RF switch 232 may enable each antenna to either deliver RF energy to the imaging chamber or to collect the RF energy from the other antennas. As shown in each of FIGS. 6A-6C, the imaging domain, D, 210 is the complex dielectric profile of the OI 205 is reconstructed.

The exemplary antenna assemblies 252 including reconfigurable antennas 254 may be used in at least two exemplary different methods of data collection schemes: a direct measurement method and an indirect measurement method. In the exemplary direct measurement method, each reconfigurable antenna 254 of the exemplary antenna assemblies 252 may operate in either transmit mode/state or receive (e.g., collect) mode/state. The transmit state may deliver electromagnetic energy from a radio frequency (RF) source to a measurement chamber 220 and may be activated by an antenna, or probe, driver circuit 230. The receive, or collect, state may sample, or collect, the scattered electromagnetic energy at a location of the reconfigurable antenna 254 when the diodes are turned on (e.g., "shorted").

The transmit/collect reconfigurable antenna 254 may be selected through a RF switch 232. After selecting a pair of reconfigurable antennas 254, the, transmit, or radiating, reconfigurable antenna 254 may illuminate the OI 205 in the measurement chamber 220 while the rest of the reconfigurable antennas 254 may receive, or collect, the scattered field. The scattered field may be measured at the location of the collector reconfigurable antennas 254. The received field by the collector reconfigurable antennas 254 may be translated into a complex number by the VNA 234 and may be directly related to the field at the location of the collector reconfigurable antenna 254. For each object 205, two sets of measurements may be obtained. First, a measurement with the presence of the object 205 inside the chamber 220 may be obtained, which is referred to as the $\vec{E}^{tot}$ or the total-field measurement. Second, a measurement with the absence of the object 205 may be obtained, which is referred to as the $\vec{E}^{inc}$ or the incident-field measurement. Subtracting the $\vec{E}^{inc}$ from the $\vec{E}^{tot}$ may result in the scattered field data used by the imaging algorithm.

In the exemplary indirect measurement methods and systems as shown in FIGS. 6B-6C, each reconfigurable antenna 254 of the exemplary antenna assemblies 252 may be used operate in either transmit, collect, or scattering modes. In these embodiments, a reconfigurable antenna 254 may be selected as a "transmitter" to illuminate the OI while another reconfigurable antenna 254 is selected as a "collector." The transmitter and collector reconfigurable antennas 254 may be activated similar to the transmitters and collectors as described in the exemplary direct method. In this exemplary indirect measurement method, a third reconfigurable antenna 254 may be activated as a scatterer, or scattering probe, and modulated by a probe driver circuit 231.

Thus, a differential scattering technique (DST) or modulated scattering technique (MST) may be used in the systems depicted in FIGS. 6B-6C.

In the indirect measurement methods, the field scattered by a scattering probe reconfigurable antenna 254 is proportional to the original field at the scattering probe reconfigurable antenna's 254 location. The collector reconfigurable antenna 254 may sample, or collect, a signal (which can be modulated) that is proportional to the field only at the scattering probe reconfigurable antenna's 254 location (see, e.g., M. Ostadrahimi, A. Zakaria, J. LoVetri, and L. Shafai, "A near-field dual polarized (TE-TM) microwave imaging system," IEEE Trans. Microw. Theory Techn., vol. 61, no. 3, pp. 1376-1384, March 2013, which may be incorporated by reference herein in its entirety). For each object, two sets of measurements may be obtained. The first measurement may be obtained with the presence of the object 205 inside the chamber 220, which is referred to as the $\vec{E}^{tot}$ or the total-field measurement. The second measurement may be obtained with the absence of the object 205, which is referred to as the $\vec{E}^{inc}$ or the incident-field measurement. Subtracting the $\vec{E}^{inc}$ from the $\vec{E}^{tot}$ may result in the scattered field data used by the imaging algorithm.

For an exemplary MST implementation as shown in FIG. 6B, the reconfigurable antennas 254 when configured as scattering probes may be successively modulated by a square waveform M(t):

$$M(t) = \frac{V_m}{2} + \frac{2V_m}{\pi}\sin(\omega_m t) + \sum_{n=3,5,...}^{\infty} \frac{2V_m}{n\pi}\sin(n\omega_m t) \qquad (1)$$

with amplitude of $V_m$ and fundamental angular frequency of $\omega_m$. The square waveform may include, or contain, harmonics of $\omega_m$, thus the probe's interaction with the field may produce various harmonics at frequencies of $\omega_{RF}\pm n\omega_m$, where n is the harmonic index. Note that the modulation frequency, $f_m$, may be significantly lower than the imaging frequency, $f_{RF}$.

Further, in MST, after a probe reconfigurable antenna 254 is modulated, the field will be perturbed or disturbed at the probe reconfigurable antenna's 254 location. The perturbed field, modulated at $f_m$, is proportional to the field at the probe reconfigurable antenna's 254 location. In order to obtain the field information, the received signal (containing $\omega_{RF}+n\omega_m$) is mixed by the in-phase (I) as well as the quadrature-phase (Q) samples of the original unperturbed RF signal 237. Note that I and Q may only contain the imaging frequency, $f_{RF}$. The output of the mixers, the IF signals, may then be precisely measured by a lock-in amplifier 239. The measured data may then be translated into the amplitude and phase of the field at the probe reconfigurable antenna's 254 location. The aforementioned data collection scheme may be repeated for each reconfigurable antenna 254 transmitter-receiver pair and for each reconfigurable antenna 254 be configured as a probe until all the data is collected.

For DST implementation as shown in FIG. 6C, the $S_{12}$ between the transmitter and the collector reconfigurable antenna 254 may be measured once when a scattering probe reconfigurable antenna 254 is in the "off" mode and once when the scattering probe reconfigurable antenna 254 is in the "on" using a VNA 234 (see, e.g., M. Ostadrahimi, P. Mojabi, S. Noghanian, L. Shafai, S. Pistorius, and J. LoVetri, "A novel microwave tomography system based on the scattering probe technique," IEEE Trans. Instrum. Meas., vol. 61, no. 2, pp. 379-390, February 2012 and see, e.g., M. Ostadrahimi, A. Zakaria, J. LoVetri, and L. Shafai, "A near-field dual polarized (TE-TM) microwave imaging system," IEEE Trans. Microw. Theory Techn., vol. 61, no. 3, pp. 1376-1384, March 2013, each of which may be incorporated herein by reference in their entireties). The relation between the measured fields at the location of a collector reconfigurable antenna 254 due to a probe reconfigurable antenna 254 and the field at the location of the probe reconfigurable antenna 254 may be similar to that explained herein.

The measurement chamber, or enclosure, 220 depicted in FIGS. 6A-6C may be a 3-D, perfect electric conductor (PEC) microwave imaging (MWI) chamber using m reconfigurable antennas. The reconfigurable antennas 254 may successively illuminate the OI 205 at a frequency of $f_{RF}$ referred to as the imaging frequency while the remaining reconfigurable antennas 254 may successively collect the field scattered by the OI 205. Thus, the reconfigurable antennas 254 may operate in a plurality of states or modes depending on what imaging methods and processes are being used: a transmit state where diodes are forward biased ("on") in this mode such that the diodes short the spacings between the printed conducting elements of the reconfigurable antenna 254; a receive state where diodes are forward biased ("on") in this mode such that the diodes short the spacings between the printed conducting elements of the reconfigurable antenna 254; a modulation state where diodes are modulated between being forward biased ("on") and reverse biased ("off"); a scattering mode where the diodes are modulated being forward biased ("on")l and a passive mode where diodes are reversed biased ("off") such that the diodes do not affect the length of the reconfigurable antenna 254 (e.g., such that the reconfigurable antennas 254 does not effect, not perturb, not disturb, etc. the electromagnetic field).

The passive mode of the reconfigurable antennas 254 may be enabled by selecting the proper number and size (e.g., length, width, depth, etc.) for the conductive portions or sections of each reconfigurable antenna 254 with respect to the $f_{RF}$. By choosing the proper number and size of the conductive portions or sections, the radiation efficiency of the reconfigurable antennas 254 configured in the passive state or mode at the desired frequency may decrease significantly at $f_{RF}$. Consequently, the "off" probe may be described as being "invisible" in the passive state or mode. In the exemplary systems, different lengths of conductive portions of the reconfigurable antennas 254 from λ/4 (quarter wavelength) to a resonance length of λ/12 (one twelfth wavelength) were tested.

As described herein, in the receive state, the switchable elements (e.g., diodes) of the reconfigurable antennas 254 may be forward biased in the direct data collection mode. Further, in DST, both the collector reconfigurable antenna 254 and the scattering probe reconfigurable antenna's 254 switchable elements may be turned "on" while, in MST, the switchable elements of the modulation probe reconfigurable antenna 254 may be modulated by the modulation square signal, denoted by M(t) (see equation (1)). The collector reconfigurable antenna 254 may sample, or collect, the impinging field.

Modeling error may be more difficult when the imaging domain 210 is inside a PEC chamber due to its high scattering properties and especial field distribution, which may be shown when comparing the field distributions provided in FIG. 8 with those in FIG. 9 for an open top circular PEC enclosure. Exemplary images of an electromagnetic field distribution in a measurement chamber about a X-Y plane for (a) $E_x$, (b) $E_y$, and (c) $E_z$ when $E_p$ is excited when only the transmitting antenna is located in the chamber is depicted in FIG. 8. Exemplary images of an electromagnetic field distribution in a measurement chamber about a X-Y plane for (a) $E_x$, (b) $E_y$, and (c) $E_z$ when $E_p$ is excited when the transmitting antenna and a plurality of additional antennas (e.g., eight total antennas) are located in the measurement chamber is depicted in FIG. 9.

As described herein, an exemplary reconfigurable antenna including a ground plane 57 is shown in FIG. 3. A ground plane 57 may be square-shaped or rectangular-shaped, and may be four times the size of an imaginary plane extending from an end region 55 of the conductive elements 56 to the RF port 59. Further, the ground plane 57 may be any shape such as a square conductor (which may be modeled). When the reconfigurable antenna 254 is in the passive mode, the reconfigurable antenna 254 may effectively not perturb the overall field distribution inside the chamber at $f_{RF}$, and thus, modeling error may be due to the difference between the experimental setup and the simple model in the inversion algorithm being kept at a minimum level.

Moreover, due to the shift in the input impedance (e.g., especially, the real part which may cause the radiation) of reconfigurable antennas in the passive (e.g., about 10 ohms) and active mode (about 36.5 ohms) at $f_{RF}$, the number of RF ports 59 can be reduced by connecting a few of the reconfigurable antennas 54 to the same RF port 59 using quarter-wave transformers ($\lambda/4$) 90 between each reconfigurable antenna 54 connected to the same RF port 59, which is shown in FIG. 7 in which the antenna assembly 52 includes for three reconfigurable antennas 54.

Based on equation (2) as shown below, when one of the reconfigurable antenna is active (e.g., as a transmitter/collector), the other two reconfigurable antennas may be configured in the passive mode. Consequently, the input impedance of the active reconfigurable antenna at the source may be about 68 ohms while he input impedance for the passive reconfigurable antennas would be about 250 ohms. Thus, even though there might be some power leakage to the passive reconfigurable antennas, most of the power would be delivered to the active antenna.

$$Z_{in} = \frac{Z_{line}^2}{Z_{antenna}} \qquad (2)$$

Because of the configurability of each reconfigurable antenna of the exemplary antenna assemblies, the reconfigurable antennas can be fabricated such that the reconfigurable antennas can be used for collecting multiple field polarizations and components. For example, the antenna assembly 52 depicted in FIG. 4 depicts one possible configuration for collecting $E_\rho$, $E_\varphi$, $E_z$, $H_\varphi$, and $H_z$.

In one or more embodiments, the highest radiation efficiency can be obtained by setting the antenna length of the reconfigurable antennas at each orientation to resonate at, e.g., a quarter-wavelength. However, when used inside a metallic enclosure, the size of these reconfigurable antennas may be reduced to provide lower profile antennas. $\lambda/12$ monopole antenna was tested inside a perfect electric conductor (PEC) chamber successfully. Exemplary reconfigurable antennas can be further reduced using one or more antenna loading and miniaturization techniques such as, e.g., meandering, capacitive and inductive loading, bending and other techniques.

Exemplary Inversion Algorithm

The goal of a MWI mathematics may be described as the reconstruction of the relative complex dielectric properties of an OI 205 denoted by $\in_r(\vec{r})$ at position $\vec{r}$ within an imaging domain 210, $\mathcal{D}$, as shown in FIGS. 6A-6C. Further, the mathematical optimization associated with quantitative MWI may be described as inherently nonlinear and ill-posed. Different algorithms and regularization techniques may be implemented for these mathematics. For an inverse mathematical problem, the OI 205 may be considered to be confined within the imaging domain 210, $\mathcal{D}$, and surrounded by transmitters and receivers on a measurement surface 220, denoted by $\mathcal{S}$. The background medium may be a homogeneous background with a known complex relative permittivity, $\in_b$. Further, the contrast of the OI 1205 may be then defined as $$\chi(\vec{r}) = (\in_r(\vec{r}) - \in_b)/\in_b \qquad (3)$$

where $\in_r(\vec{r})$ is the complex relative permittivity of the OI 205. Outside the imaging domain 220, $\mathcal{D}$, $\chi=0$. Further, the background and OI 205 are assumed non-magnetic, i.e., the background and OI have a relative permeability $\mu_r=1$.

The calibrated data may inverted using an exemplary contrast source inversion algorithm (CSI) (see, e.g., P. Van Den Berg and R. Kleinman, "A contrast source inversion method," Inverse problems, vol. 13, p. 1607, 1997, which is incorporated herein by reference in its entirety) formulated using an exemplary finite element method (FEM) (see, e.g., A. Zakaria, C. Gilmore, and J. LoVetri, "Finite-element contrast source inversion method for microwave imaging," Inverse Probl., vol. 26, no. 11, p. 115010, November 2010; A. Zakaria and J. LoVetri, "The finite-element method contrast source inversion algorithm for 2d transverse electric vectorial problems," IEEE Tran. Antenn. Propag., vol. 60, no. 10, pp. 4757-4765, October 2012, each of which is incorporated herein by reference in their entireties) or an exemplary Gauss-Newton inversion method (see, e.g., P. Mojabi, J. LoVetri, and L. Shafai, "A multiplicative regularized gauss-newton inversion for shape and location reconstruction," Antennas and Propagation, IEEE Transactions on, vol. 59, no. 12, pp. 4790-4802, December 2011, which is incorporated herein by reference in its entirety). Both exemplary algorithms may iteratively update $\in_r(\vec{r})$ until a match (e.g., best match) is obtained between the numerically calculated field scattered by the OI 205 with that collected, then calibrated, from the exemplary measurement system. A flow chart of an exemplary algorithm is presented in FIG. 10

The exemplary inversion processes and algorithms described herein may not fully model the exemplary imaging system, e.g., due to a heavy computational cost. Thus, the data collected from the exemplary imaging system may be calibrated. The task of calibrating an exemplary imaging system may be dependent on the imaging system configuration. Several calibration techniques may be used such as, e.g., using the incident-field, or using the scattered-field of a known reference object, such as a perfect electric conductor (PEC). In at least one embodiment, scattered field calibration may be used. Also, in at least one embodiment, incident-field calibration may be used for a PEC-enclosed microwave imaging system.

For multi-polarized scenarios, each polarization can be calibrated separately for the chosen source models or using the same source model as that of the normal source to the PEC enclosure for a PEC-enclosed MWI system. The former may be possible because the system is operated at a frequency where multiple modes exist. Also, all field components may "get excited" inside a PEC enclosure as shown in FIG. 8.

Exemplary Air-Background Prototype

Figure 11:
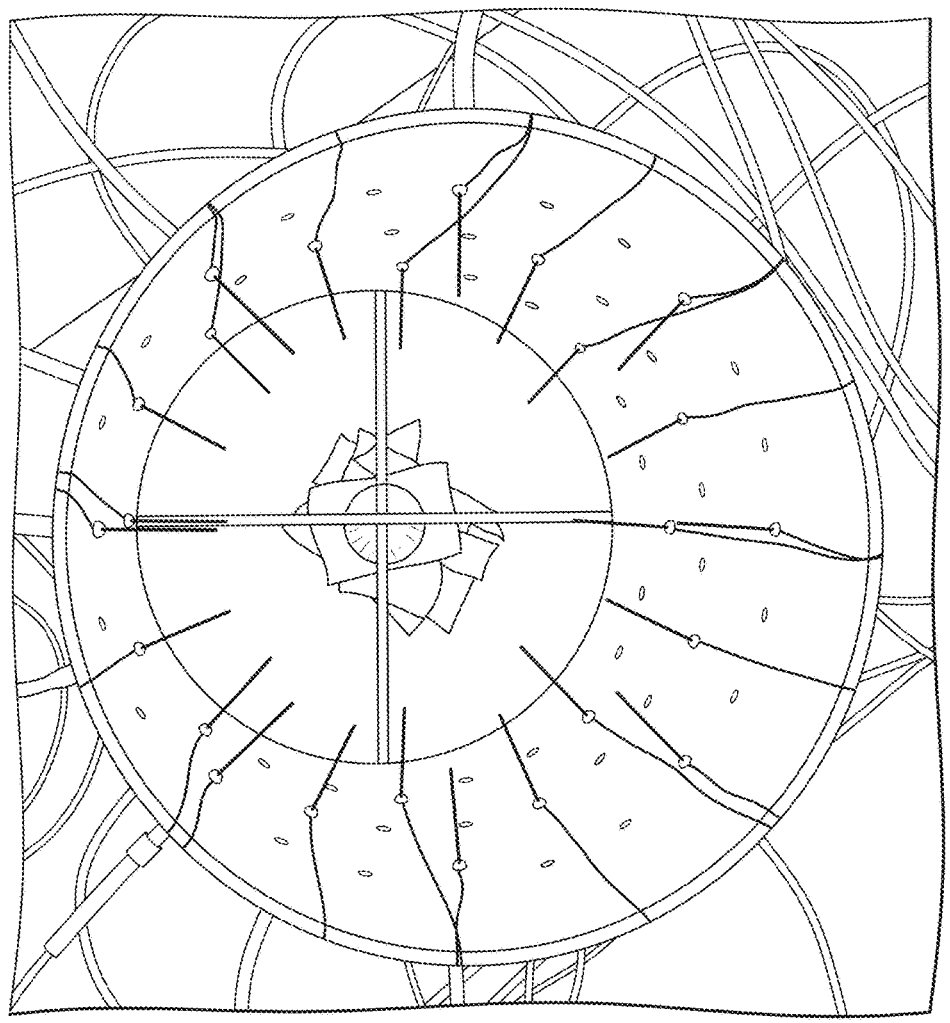
FIG. 11 is a top-down photograph of an exemplary measurement chamber of an imaging system.
Figure 12A:
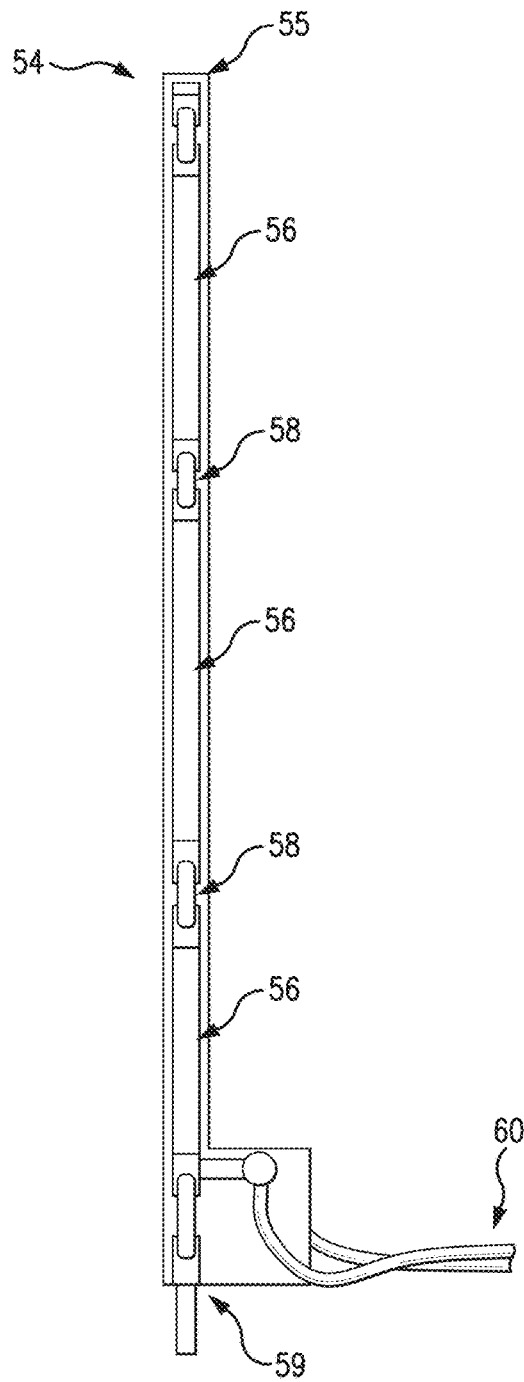
FIGS. 12A-12B is front and back, respectively, photographs of an exemplary reconfigurable antenna for use with the systems, apparatus, and methods described herein.
Figure 12B:
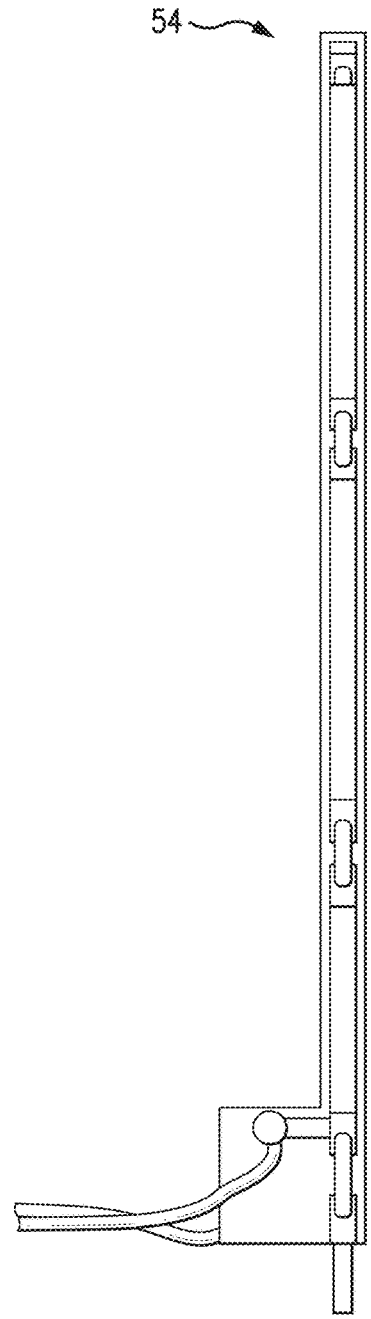

A prototype MWI system with a PEC enclosure was manufactured with air as the background medium as shown in the photograph of FIG. 11. The prototype system included twenty-four reconfigurable antenna assemblies equally distributed in three vertical layers in an open top circular PEC enclosure with a radius of 15.8 centimeters (cm) and height of 31 cm. Each reconfigurable antenna assembly included a single antenna. Each antenna included 5 P-I-N diodes on a double layer printed circuit board (PCB). Further, each antenna also included two capacitors and resistors and a pair of twisted wires for DC coupling and decoupling. A photograph of the exemplary antenna assembly 54 is shown in FIG. 12A-12B. Specifically, a first, or front, side of the antenna assembly 54 is shown in FIG. 12A, and a second, or back, side (opposite the first, or front, side) of the antenna assembly 54 is shown in FIG. 12B. The cutoff frequency for the exemplary chamber of FIG. 11 was found to be 556 megahertz (MHz). Further, the frequency at which the inversions are presented herein was at 1.748 gigahertz (GHz), which was selected using an exemplary comparison technique.

Figure 13:
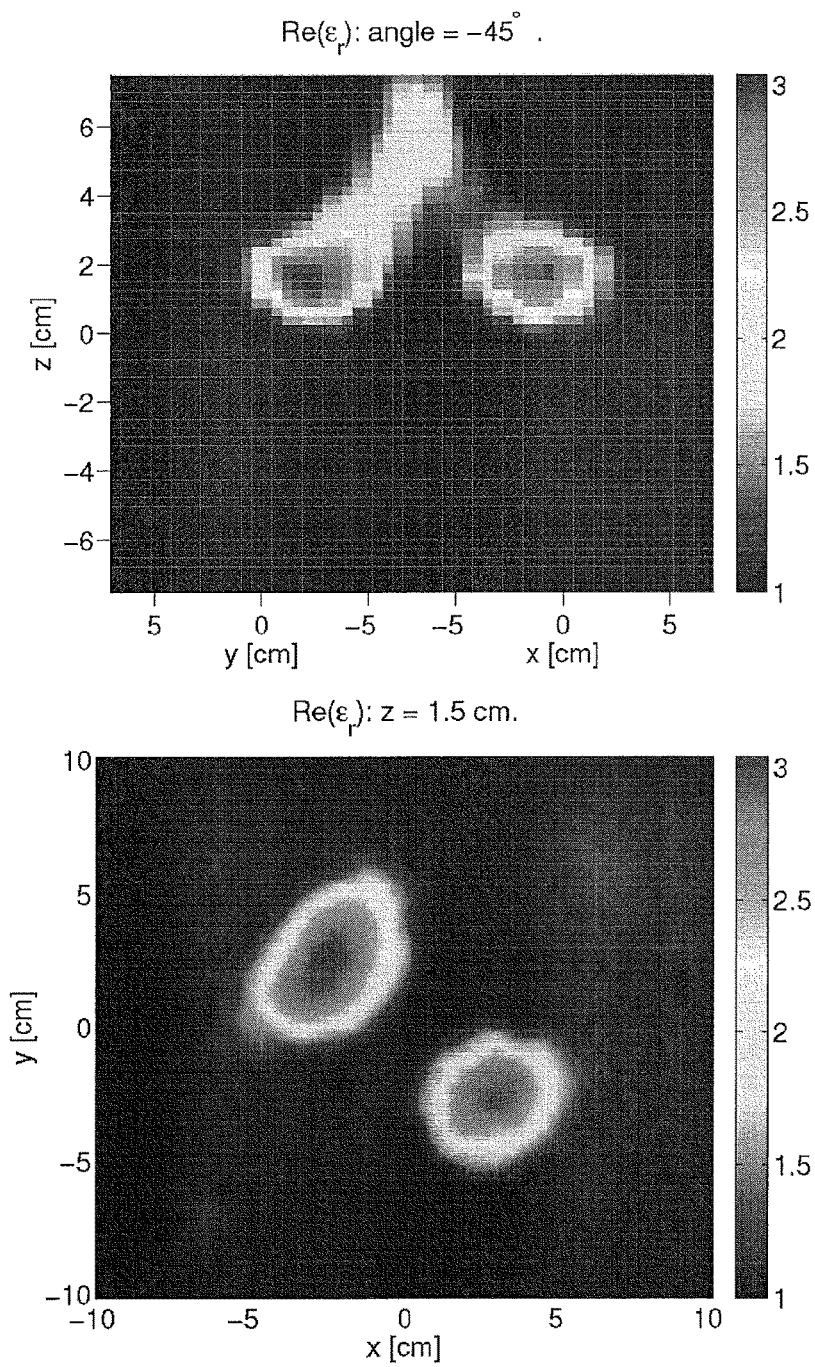
FIG. 13 are the real parts of the dielectric permittivity of an exemplary reconstructed image of two nylon blocks.
Figure 14:
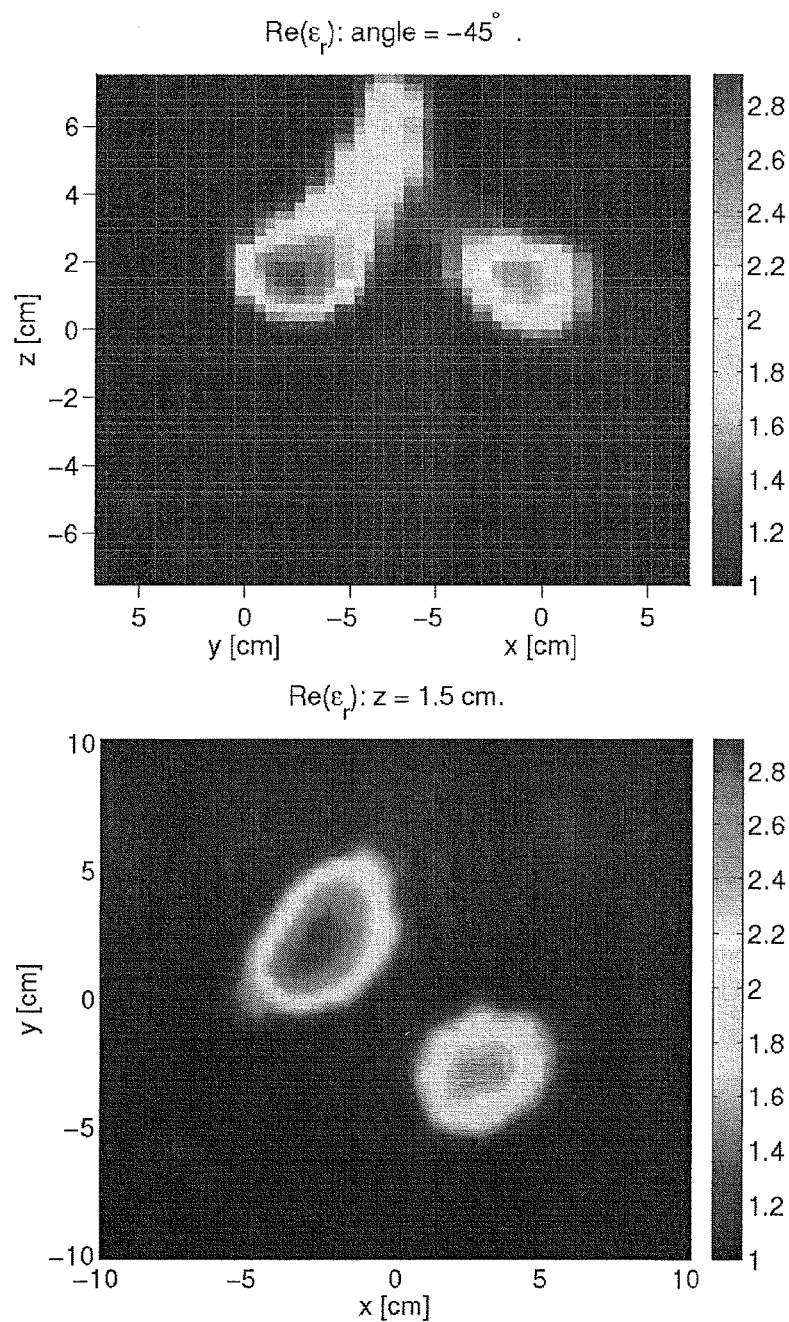
FIG. 14 are the real parts of the dielectric permittivity of an exemplary reconstructed image of a nylon block and a wood block.

At 1.748 GHz, more than 15 different modes may be excited inside the chamber. Different sets of data were collected for various objects such as, e.g., a 3.8 cm diameter by 5.3 cm height nylon rod or cylinder, a 4.5 cm by 3.8 cm by 4.9 cm wood block, etc. In one example, datasets were collected using all antennas as transmitters and collectors, the measured data was calibrated using incident field calibration technique, and the multiplicatively regularized CSI (MR-CSI) algorithm was utilized to invert the collected data. Imaging results are shown in FIGS. 13-14. Two nylon blocks were imaged at 1.749 GHz, and the image reconstruction of the two nylon blocks is depicted in FIG. 13. More specifically, the real parts of $\in_r$ at φ=−45 degrees and at z=1.5 cm are depicted in FIG. 13. A nylon block and a wood block were imaged at 1.749 GHZ, and the image reconstruction of the two blocks is depicted in FIG. 14. More specifically, the real parts of $\in_r$ at φ=−45 degrees and at z=1.5 cm are depicted in FIG. 14. In these examples, each transmitter had 23 measurement points since no data was collected at the location of the transmitter itself.

Figure 15:
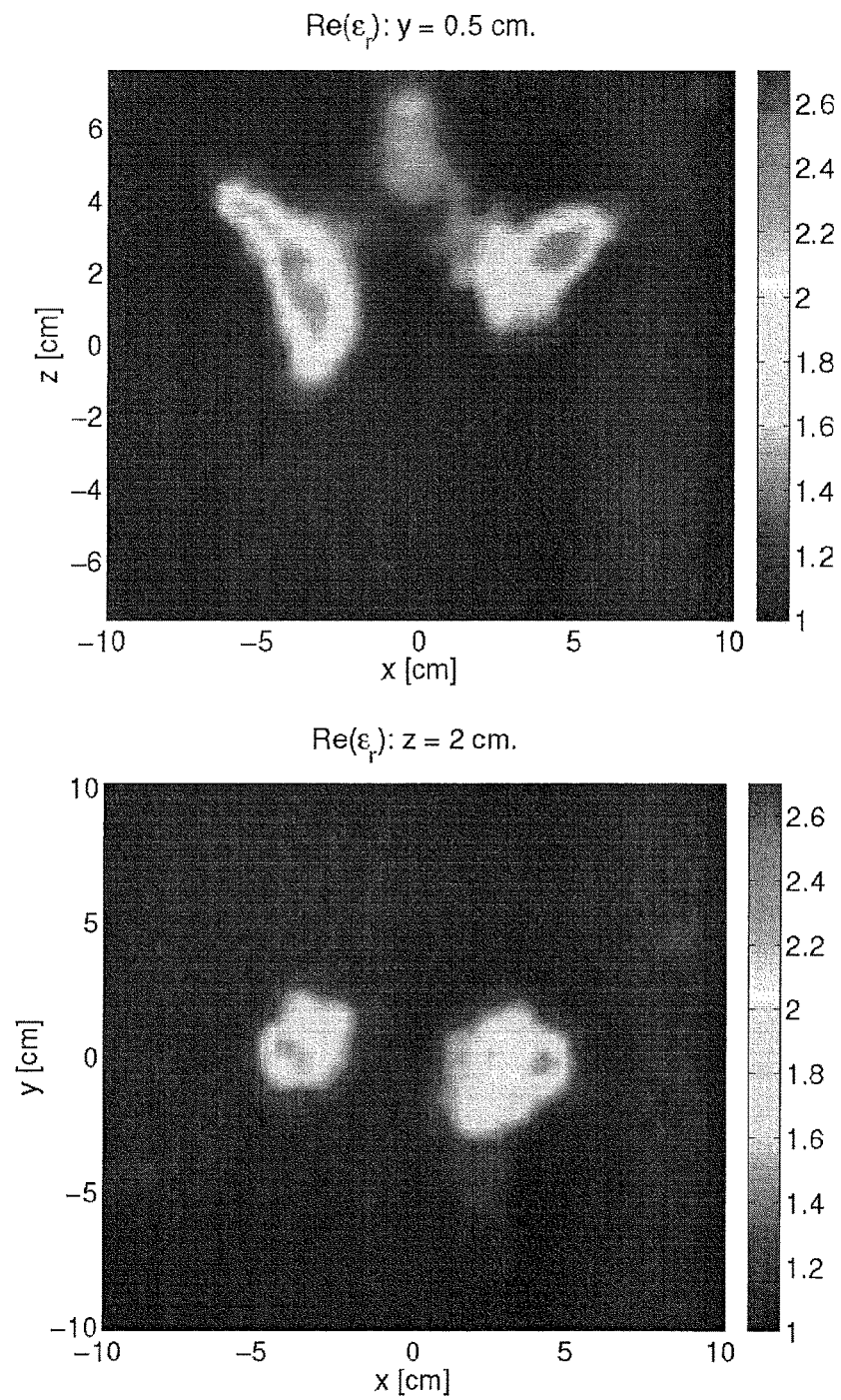
FIG. 15 are the real parts of the dielectric permittivity of an exemplary reconstructed image of two nylon blocks.

In the second example, datasets were collected using four antennas per each of three vertical layers for a total of 12 antennas as transmitters and collectors and 4 additional antennas per vertical layer were used as scattering probes for DST. Similar to the previous example, the measured data was calibrated using incident field calibration technique and MR-CSI was used to invert the measured data. Two nylon blocks were imaged at 1.749 GHz, and the image reconstruction of the two nylon blocks in depicted in FIG. 15. More specifically, the real parts of $\in_r$ at y=0 cm and at z=2.0 cm are depicted in FIG. 15. In this example, there were 23 measurement points for each transmitter.

Figure 16:
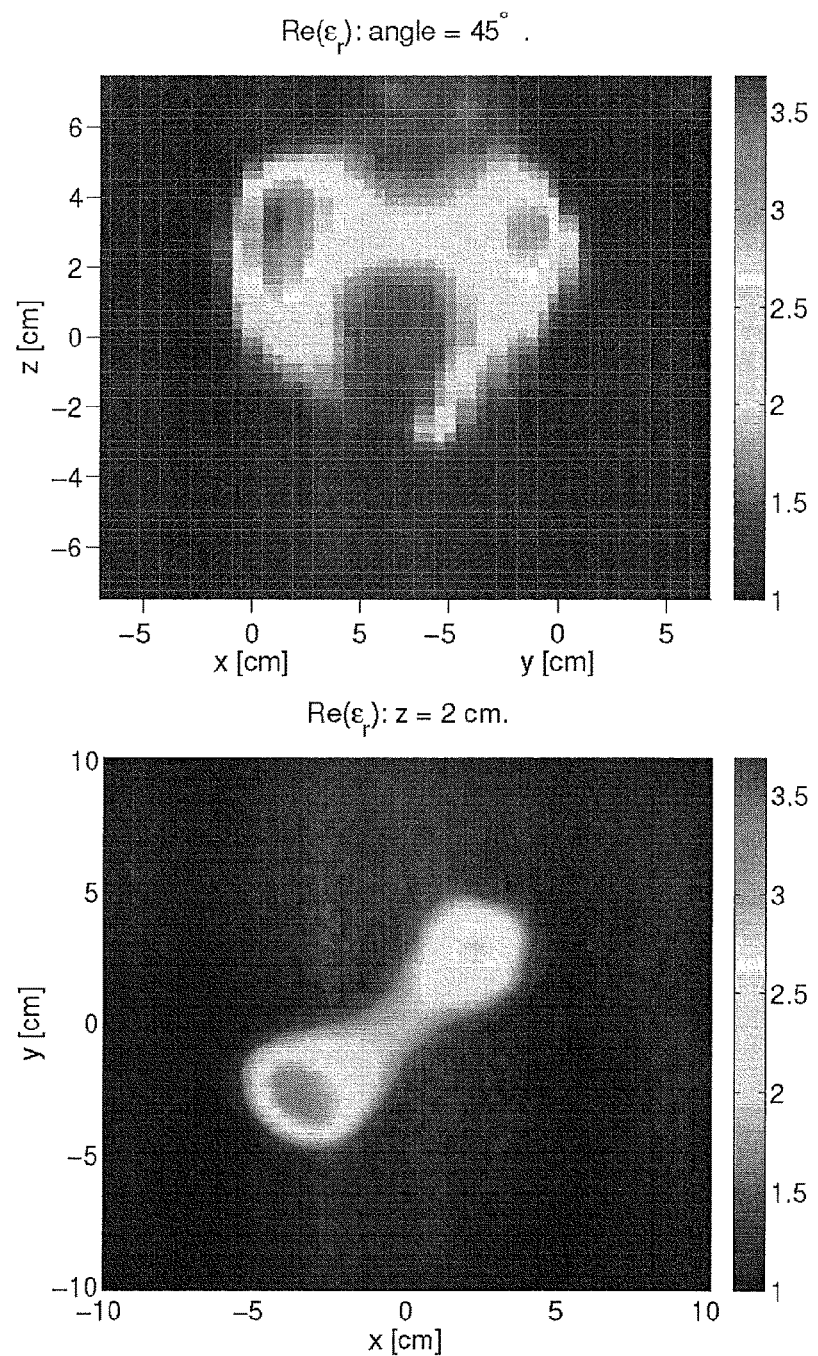
FIG. 16 are the real parts of the dielectric permittivity of an exemplary reconstructed image of two nylon blocks.
Figure 17:
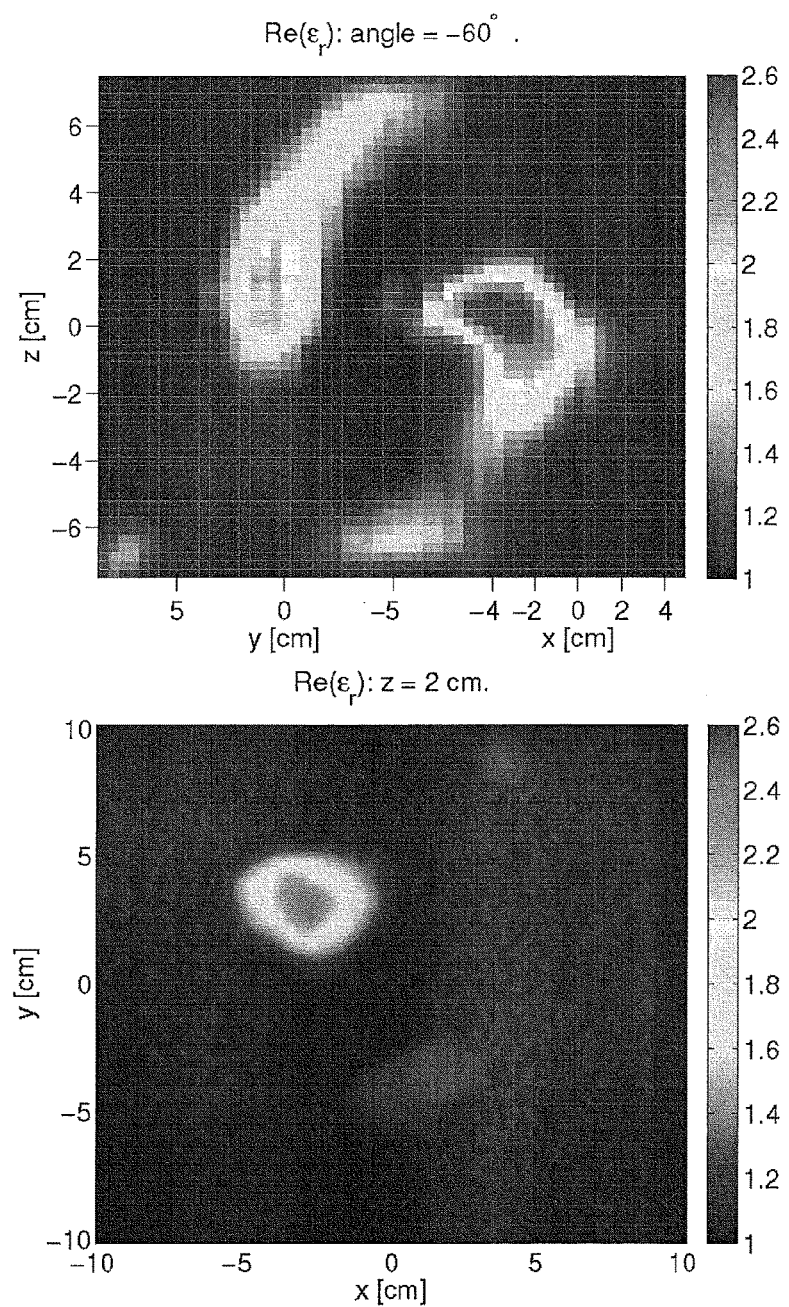
FIG. 17 are the real parts of the dielectric permittivity of an exemplary reconstructed image of two nylon blocks at different heights.

Additionally, to test the performance of MWI system for exemplary antennas, λ/12 monopoles were used as transmitters and collectors to image two nylon cylinders having 1.5 inch diameters. The inversion results obtained for this example are shown in FIG. 16. More specifically, the real parts of $\in_r$ at φ=45 degrees and at z=2 cm are depicted in FIG. 16. In this example, all 24 antennas were used as transmitters and receivers similar to the first example. Use of reconfigurable antennas was also tested when the chamber is covered with a PEC-cap to form a completely resonant chamber as shown in FIG. 17. More specifically, the real parts of $\in_r$ at φ=−60 degrees and at z=2 cm are depicted in FIG. 17. Using the frequency selection technique described herein, the appropriate frequency for this example was found to be 1.419 GHz at which over 38 modes may be excited inside the chamber. Further, a resonant cavity may be more sensitive to any perturbation in the chamber. Thus, when non-reconfigurable antennas are used, the mismatch between the numerical model and the measurement system may increase.

Thus, as described herein with respect to the examples, the reconfigurable antennas can be adopted in a certain configuration to reduce the number of RF ports. Further, MST-based measurement may suppress noise and phase error due to potential stress on the cables, the RF multiplexer, and/or measurement instruments because, e.g., the cables remain stationary during the modulated data collection and the effect of the cables on the measurement may, therefore, be negligible. Also, phase error that may be due to different RF routings of the RF multiplexer may effectively vanish. Thus, the exemplary systems may no longer be sensitive to cable length as well as the configuration of the RF multiplexer. Further, the exemplary antenna assemblies may be fabricated on PCB technology, which is widely available, and can be fabricated with high degree of accuracy (e.g., due to the PCB technology). Due to the presence of the PEC chamber, the biasing wires may not interfere with the data collection and may make the numerical model sophisticated (e.g., because of being shielded by the "ground" plane).

Further, collecting different field polarizations with previously-existing MWI systems may require a sophisticated design. The exemplary systems described herein may collect and illuminate different polarizations including vertical, horizontal, and normal polarizations.

As described herein, the exemplary antennas can be used as either electric field probes or magnetic field probes. The exemplary systems can be accurately modeled by an exemplary inverse algorithm due to the presence of the well-defined boundaries of the imaging chamber as well as use of reconfigurable antennas. Further, the exemplary antennas can be of any shape and different miniaturization techniques can be adopted to reduce the size of the exemplary antennas. Additionally, multiple antennas can be cascaded by the means of coaxial cables or any PCB routed transmission lines to reduce the number of RF ports.

The measurement, or imaging, chamber can be filled with any material such as matching fluids. The system can also be used for detection of anomalies in a relatively homogenous media. It may be useful to use the exemplary system with PEC chambers of different sizes and shapes.

For instance, the exemplary systems can be adapted for breast cancer screening. The measurement/imaging chamber can be attached to a bed, and a woman may rest in prone position on the bed while positioning her breast into the measurement/imaging chamber. The chamber can be filled with a matching fluid such as water glycerin solution. The antenna assemblies may then be used to illuminate the object, i.e., the breast, from different locations by different polarizations while the remaining antennas of the antenna assemblies collect the scattered field using, e.g., any of the exemplary mentioned techniques/processes/methods described herein. Once the data acquisition is completed, the data may be calibrated and processed for image reconstruction.

Electromagnetic imaging inside chambers with metallic walls may be advantageous. Potential advantages in utilizing these chambers may include the following: shielding the inside of the imaging chamber from outside noise; better signal-to-noise ratio that may improve the resolution of the imaging modality; less complex system modeling in comparison to open-boundary problems; and the ability to use a lossless matching medium which means more energy is delivered to the target.

As described herein, one or more exemplary electromagnetic imaging systems and methods may use boundary condition apparatus such as, e.g., metallic enclosures. For example, the exemplary systems and methods may utilize normal field component measurements near the metallic chamber walls to perform imaging. Further, for example, near the chamber boundary, the normal electric field components may be dominant while the tangential components vanish.

The exemplary systems and methods may use a parallelized full-vectorial electromagnetic finite-element solver and various different chamber configurations that may be modeled used to collect synthetic datasets. The data may be inverted using an exemplary finite-element contrast source inversion (FEM-CSI) method, and normal electric field data may be collected from two or more configurations. One exemplary imaging setup may include an air-filled circular metallic chamber with an open-top and, within the chamber, 24 antennas may be distributed in three vertical layers that are used to measure the normal electric field component near the chamber walls using 12 monopole antennas normal to the bin walls. Another exemplary imaging setup may provide electromagnetic imaging inside a grain-bin storage facility. In at least one embodiment, the grain bin may be an enclosed metallic chamber having a 4.7 meter radius and a 7.5 meter height.

Storage of large amounts of grain post-harvest is common during drying, distribution, and preservation of crops. During storage, where grain is usually held in a large metallic container or bin, changes in temperature, moisture, and insect infestation can cause grain to spoil, annual post-harvest crop losses are estimated up to 30% in some countries.

The exemplary grain-monitoring systems and methods using microwave imaging described herein may overcome the deficiencies of existing sensor technology and may allow farmers and distributors a robust way to preserve food stores and increase revenue. The exemplary systems and methods may be described as aiming to produce global, quantitative images of grain properties throughout the bin from measurements taken by side-mounted antennas used to interrogate the bin contents.

The exemplary systems and methods can also be adopted in grain bin monitoring where the imaging domain is surrounded by a conducting material such as, e.g., steel, to monitor the condition of the grain located in the bin during storage and to detect grain spoilage. Further, the exemplary systems and methods can also be used to detect the grain level without the need for any additional sensors.

Grain Bin Example

Grain products are stored after harvest, and spoilage (losses) happen to the grain during storage due to, e.g., changes in temperature, changes in humidity, changes in moisture content, external agents (e.g., insects, fungi, pests, etc.). Exemplary microwave imaging (MWI) systems, apparatus, and methods may be applied to image grain in grain bin. As described herein, MWI results in an image of dielectric properties. Further, MWI imaging of grain in grain bins may provide qualitative localization, provide quantitative reconstruction of grain's electric properties, provide data that can be converted to moisture and/or temperature, use side-mounted antennas that may not need reinforcement, and be globally sensitive.

The scattered-field formulation may be represented by the following:

$$j\omega \epsilon_b \vec{E}^{sct}(\vec{x}) - \nabla \times \vec{H}^{sct}(\vec{x}) = -\vec{w}^{\epsilon}(\vec{x}) \tag{4}$$

and $$j\omega \mu_b \vec{H}^{sct}(\vec{x}) - \nabla \times \vec{E}^{sct}(\vec{x}) = -\vec{0} \tag{5}$$

The contrast sources may be represented by the following:

$$\vec{w}^{\epsilon} \triangleq j\omega \epsilon_b \chi^{\epsilon}(\vec{x}) \vec{E}^{tot}(\vec{x}). \tag{6}$$

The contrast $\chi^{\epsilon}$ may use the background $\epsilon_b$ as shown in the following:

$$\chi^{\epsilon}(\vec{x}) \triangleq (\epsilon(\vec{x}) - \epsilon_b)/\epsilon_b. \tag{7}$$

The goal may be described as determining the $\epsilon(\vec{x})$ inside the bin.

For $N_t$ transmitters, $$\mathcal{F}^{CSI}[\vec{w}_t^{\epsilon}, \chi^{\epsilon}] = \eta_S^E \sum_{t=1}^{N_t} \|\vec{\rho}_t^E\|_S^2 + \eta_D^E \sum_{t=1}^{N_t} \|\vec{r}_t^E\|_D^2. \tag{8}$$

The data error may be modeled by the following:

$$\vec{\rho}_t^E(\vec{x}) \triangleq \vec{E}_t^{sct,data}(\vec{x}) - \mathcal{L}_S^{E_\epsilon} \vec{w}_t^{\epsilon}(\vec{x}'). \tag{9}$$

And the domain error may be modeled by the following:

$$\vec{r}_t^E(\vec{x}) \triangleq \chi^{\epsilon}(\vec{x}) \left( \vec{E}_t^{inc}(\vec{x}) + \mathcal{L}_D^{E_\epsilon} \vec{w}_t^{\epsilon} \right) - \vec{w}_t^{\epsilon}(\vec{x}). \tag{10}$$

In an exemplary imaging setup or system, antenna assemblies including simple monopole antennas to be side-mounted to the bin walls may be used. Further, a VNA may be used to drive and/or receive field data, e.g., similar to the systems depicted in FIGS. 6A-6C.

Figure 20:
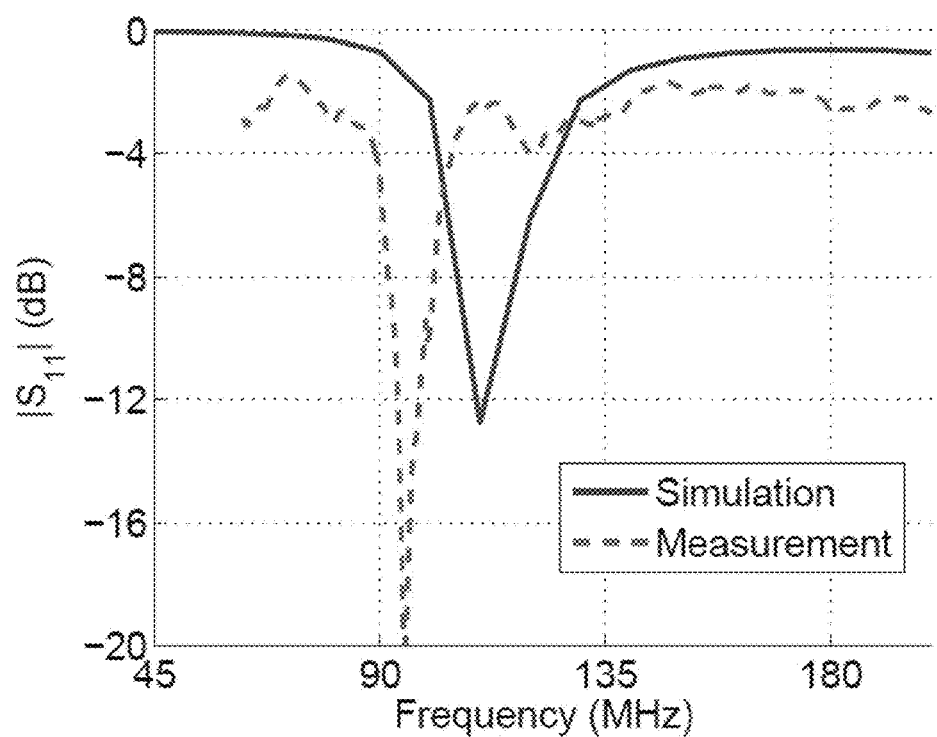
FIG. 20 is a graph of a simulated and measure radiation pattern of an exemplary antenna.

For example, using a center frequency of 100 MHz in air, a wooden base for mechanical support, and a threaded 1 cm (diameter) steel rod for endurance in high pressure conditions in the grain bin to simulate an exemplary monopole antenna, the normal component of the electromagnetic field was collected. The radiation pattern of the exemplary monopole antenna is shown in FIG. 20.

Figure 18:
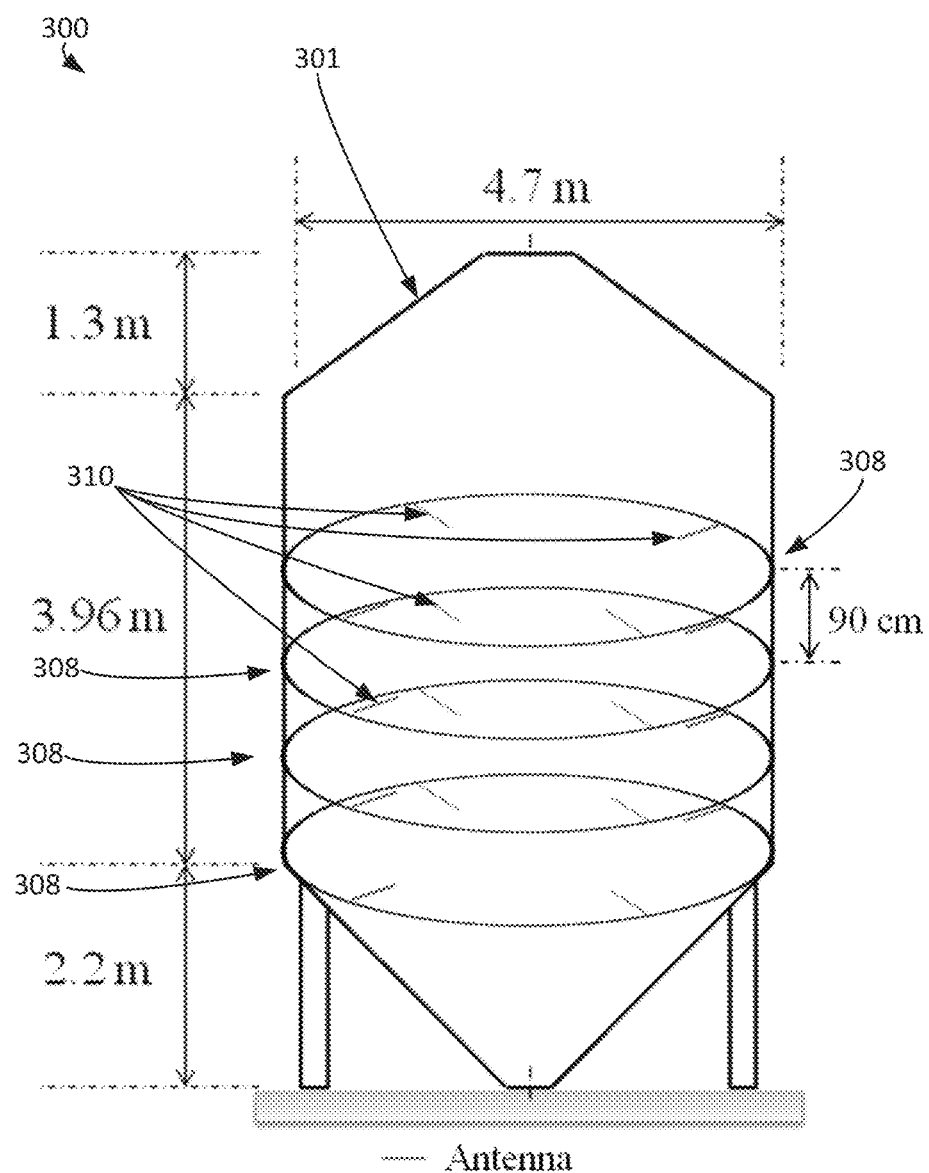
FIG. 18 is a diagrammatic representation of an exemplary imaging system for use with a grain bin.
Figure 19:
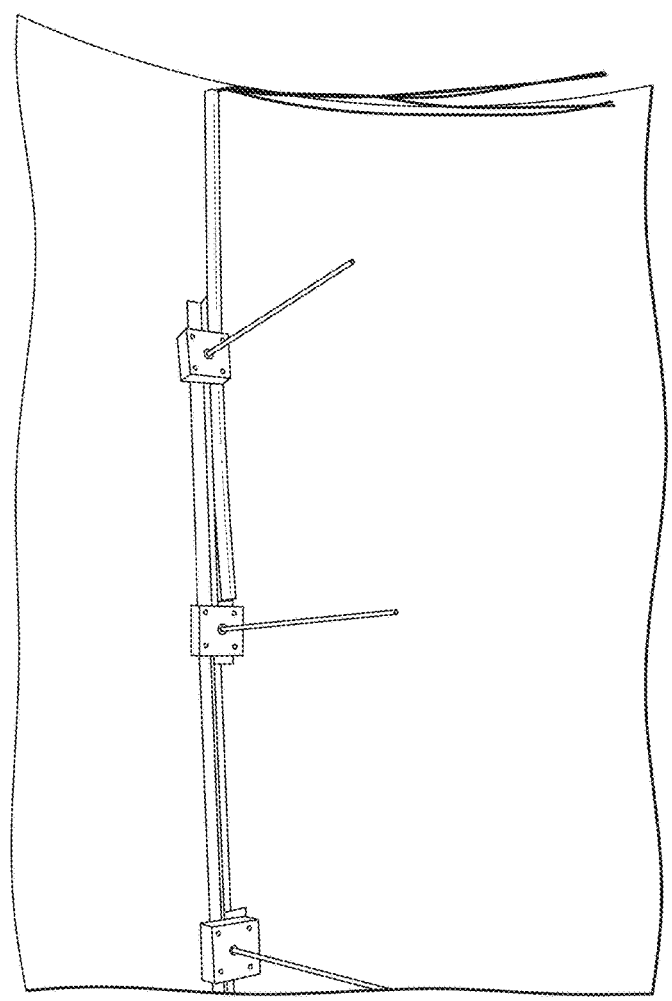
FIG. 19 is a photograph of a plurality of exemplary antennas in a grain bin.

An exemplary imaging system 300 including a plurality of antenna assemblies 310 dispersed in vertical layers 308 about a metallic grain bin 301 is depicted in FIG. 18. Further, a photograph of an exemplary antenna assembly 310 in the grain bin 301 is shown in FIG. 19.

Figure 21:
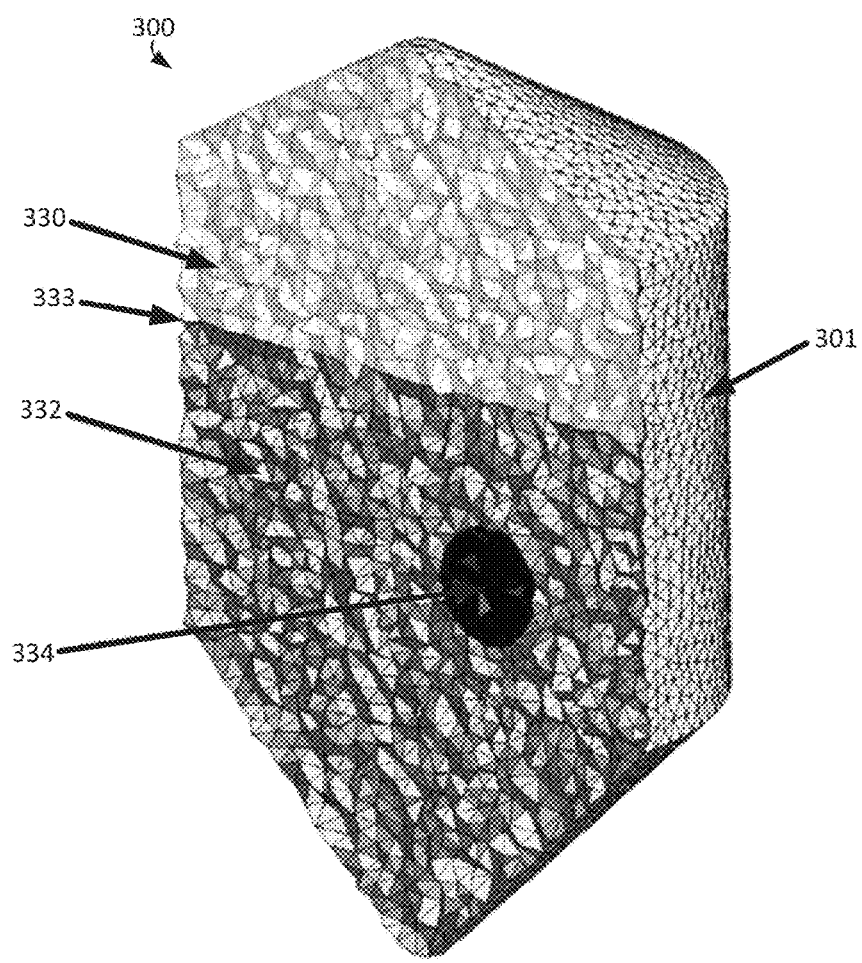
FIG. 21 is an unstructured mesh model of the measurement chamber, i.e., a grain bin.
Figure 22:
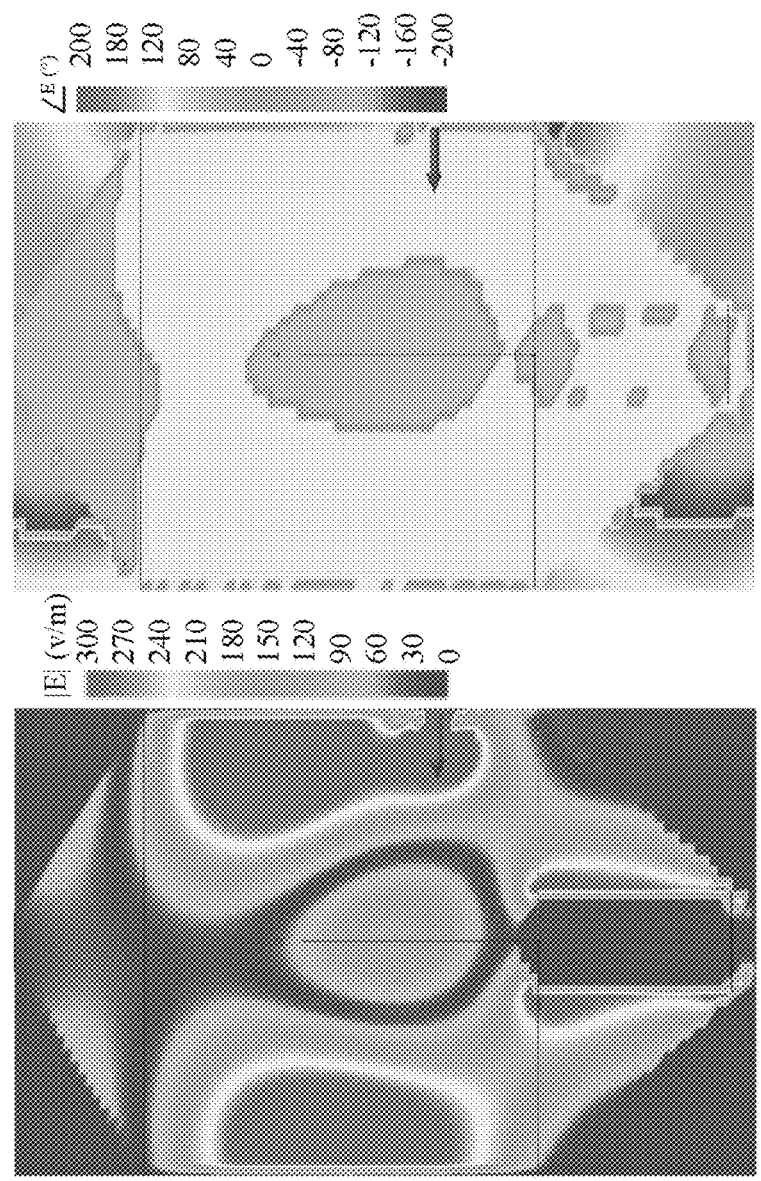
FIG. 22 are exemplary images of an electromagnetic field distribution in the measurement chamber of FIG. 21 with the transmitting antenna and a plurality of additional antennas included in the model.
Figure 23:
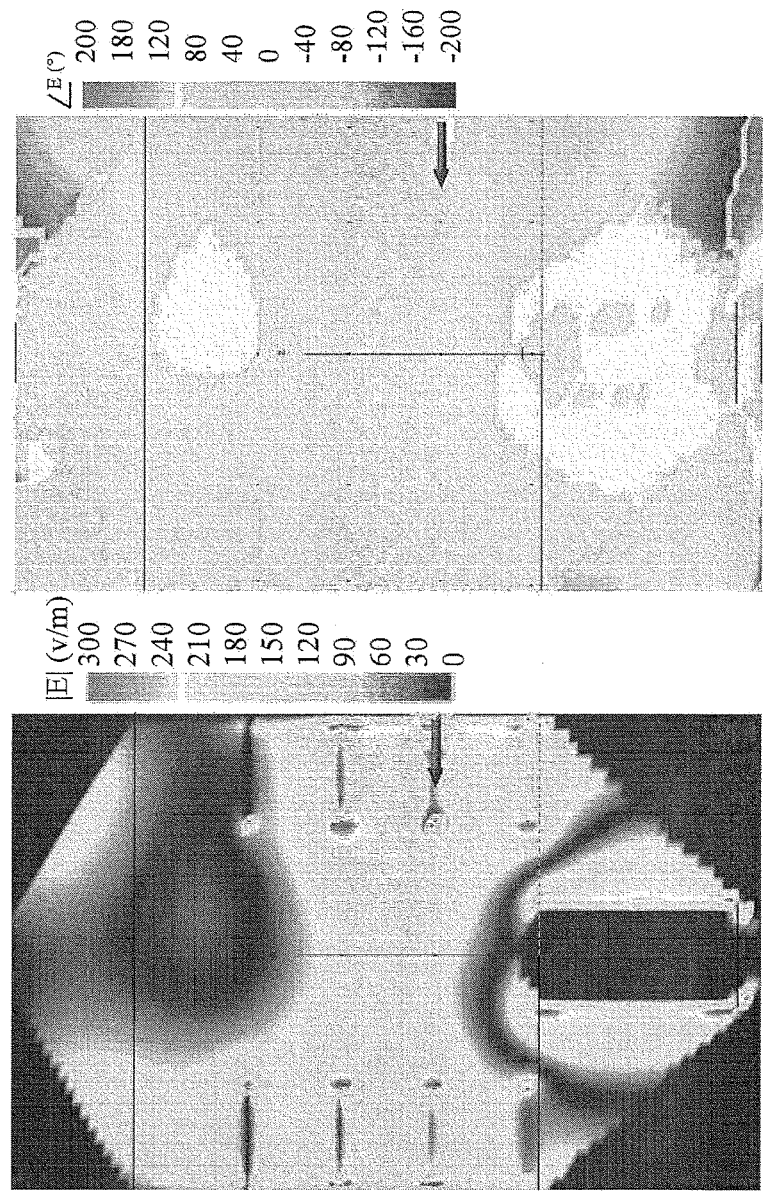
FIG. 23 are exemplary images of an electromagnetic field distribution in the measurement chamber of FIG. 21 without antennas including the model.

The FEM-CSI may use an unstructured mesh obtained from CAD model of the bin as shown in FIG. 21. As shown, the FEM-CSI may model free space 330, dry grain 332, and spoiled grain 334. Further, the FEM-CSI may support ideal dipole sources. The magnitude and phase of the field distribution inside the grain bin 301 with the monopole antennas in the model are depicted in FIG. 22 and without antennas included in the model are depicted in FIG. 23.

A variety of exemplary calibration processes may be used in the exemplary systems, methods, and apparatus. For example, in an incident field calibration process, an incident field measurement may be taken with an empty chamber ($U^{inc}$). Then, a total field measurement in presence of reference object ($U^{tot,\ ref}$) may be taken. And lastly, a total field measurement in presence of object-of-interest ($U^{tot,\ OI}$). Further, for example, in a scattered field calibration process, an incident field measurement may be taken with an empty chamber ($U^{inc}$). Then, a total field measurement in presence of reference object ($U^{tot,\ ref}$) may be taken (which, e.g., could be grain-level). And lastly, a total field measurement in presence of object-of-interest ($U^{tot,\ OI}$).

For a field component v, the calibrated field at rth receiver due to the tth transmitter:

$$E_{v,t,r}^{sct,cal} = \frac{U_{v,t,r}^{tot,OI} - U_{v,t,r}^{inc}}{U_{v,t,r}^{tot,ref} - U_{v,t,r}^{inc}} E_{v,t,r}^{sct,ref} \quad (11)$$

where $E_{v,t,r}^{sct,\ ref}$ is the analytic scattered field from the reference object.

For frequency selection, synthetic data for a conducting sphere for a frequency range of 50 MHz to 100 MHz and the incident field calibrated measurement data for the conducting sphere for a frequency range of 50 to 100 MHz may be used.

$$\text{Diff}(f,Tx,Rx) = \|E_{Tx,Rx}^{FEM} - E_{Tx,Rx}^{Measured}\| \quad (12)$$

Figure 24:
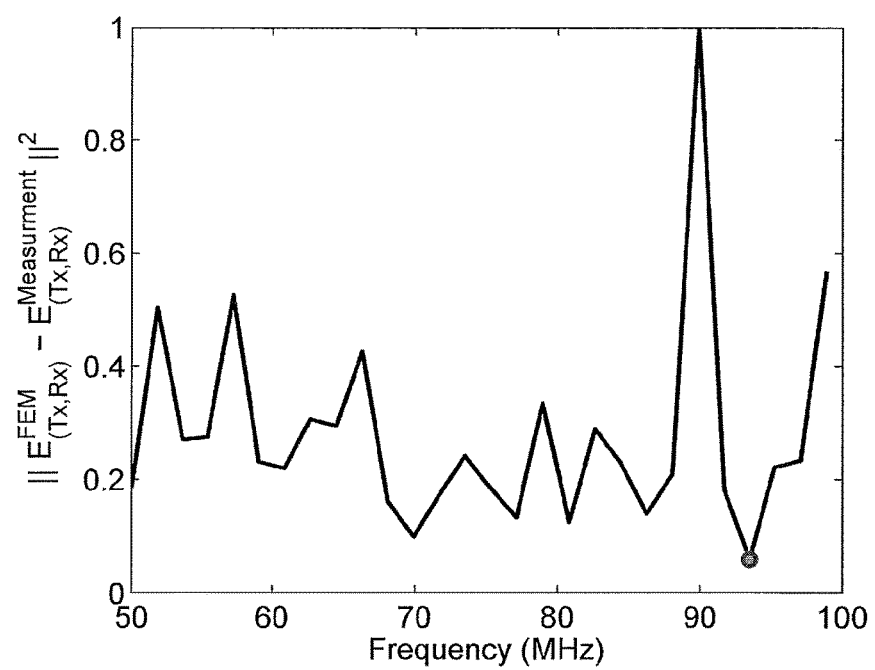
FIG. 24 is a graph of the norm of the difference between measured and finite element model (FEM) data sets as a function of frequency.

The norm of the difference between measured and FEM data sets as a function of frequency as shown in FIG. 24.

For the experimental setup, the grain bin 301 was filled with hard red winter wheat 332 in which all antennas 310 were buried. 17.2 kg of a hard red winter wheat and water mixture in a bucket was used to simulate spoiled grain 334. 8.82% of the weight of the mixture was water. A conducting sphere with a diameter of 62 cm was used as the reference object for frequency selection and calibration. Further, an incident field calibration was performed with the bin 301 filled with wheat 332. Still further, an inversion domain was set to be the whole bin 301 up to an approximate of the grain level 333 inside the measurement bin 301. The simulated-spoiled grain 334, e.g., the bucket, was buried between antenna columns 1 and 2, and detection of the location of the simulated-spoiled grain 334 is shown the exemplary reconstructed images of FIG. 25. The simulated-spoiled grain 334, e.g., a bucket, was buried between antenna columns 1 and 4 and detection of the location of the simulated-spoiled grain 334 is shown the exemplary reconstructed images of FIG. 26. The artifacts may be due to modeling errors.

Figure 25:
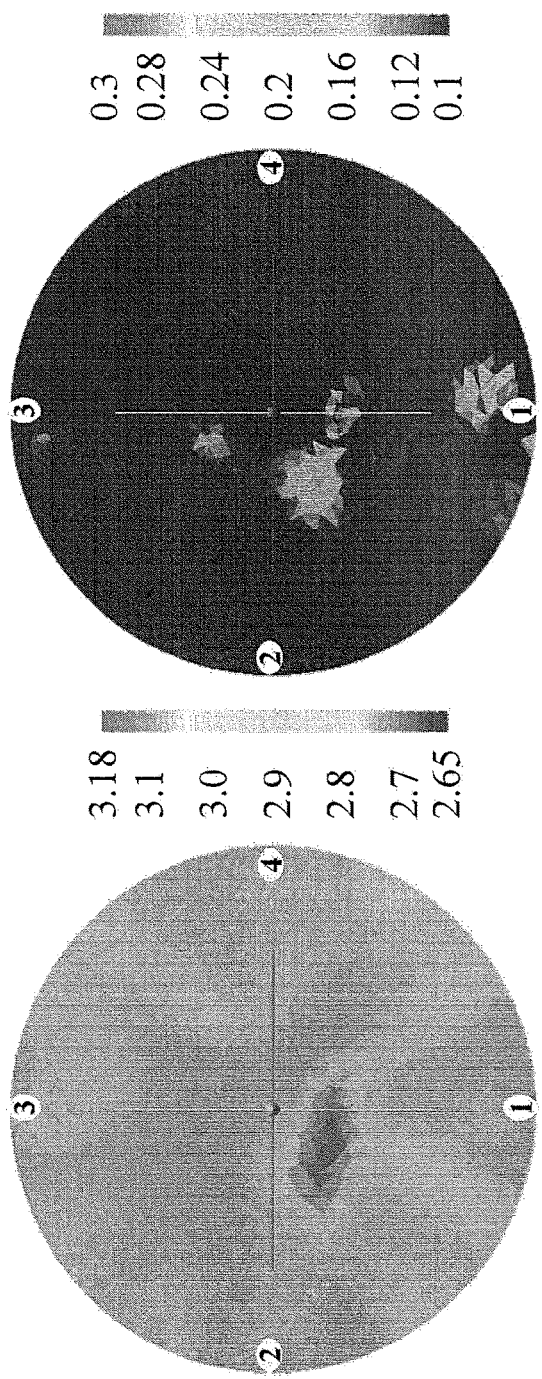
FIG. 25 are exemplary reconstructed images of an object located within grain in the measurement chamber of FIG. 21.
Figure 26:
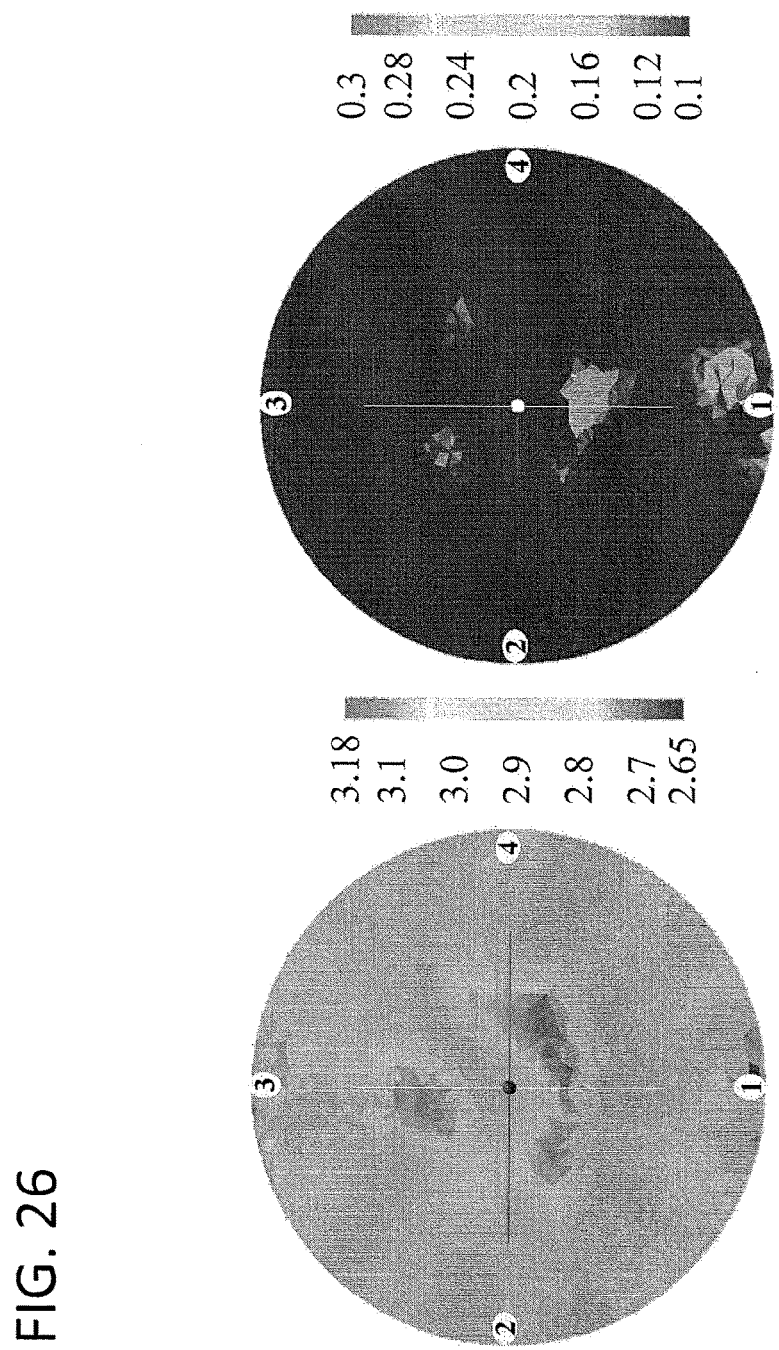
FIG. 26 are exemplary reconstructed images of the object located within grain in a different location than FIG. 25 in the measurement chamber of FIG. 21.
Figure 27:
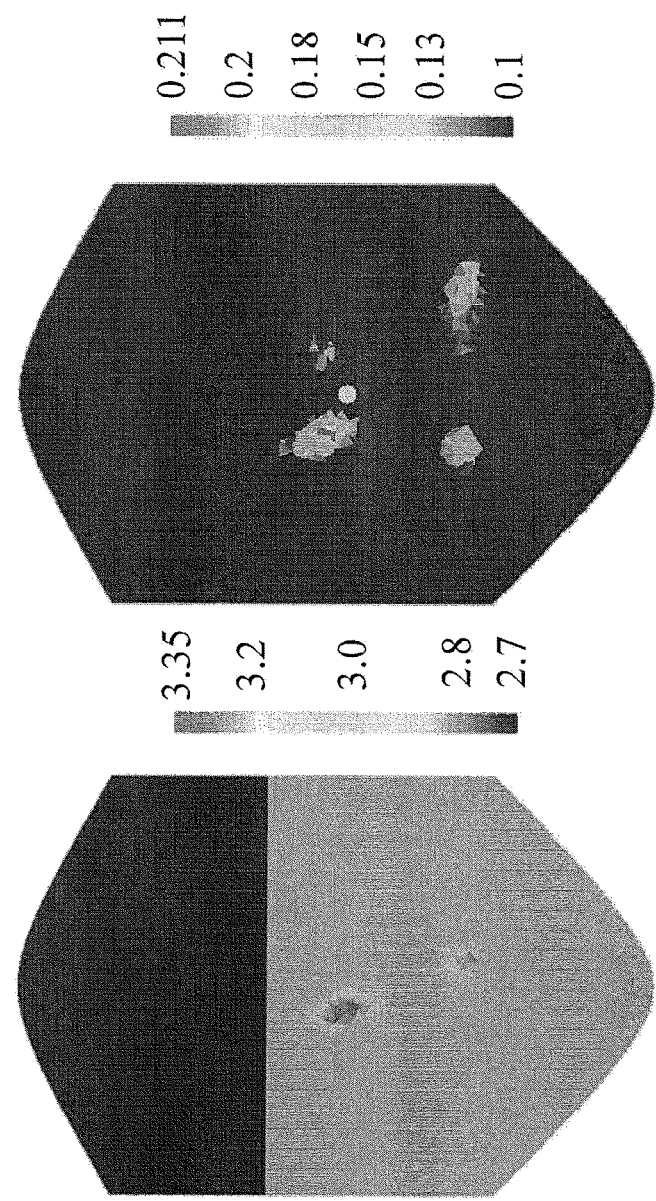
FIGS. 27-28 are exemplary reconstructed images of the object located within grain in a different location than FIGS. 25-26 in the measurement chamber of FIG. 21.
Figure 28:
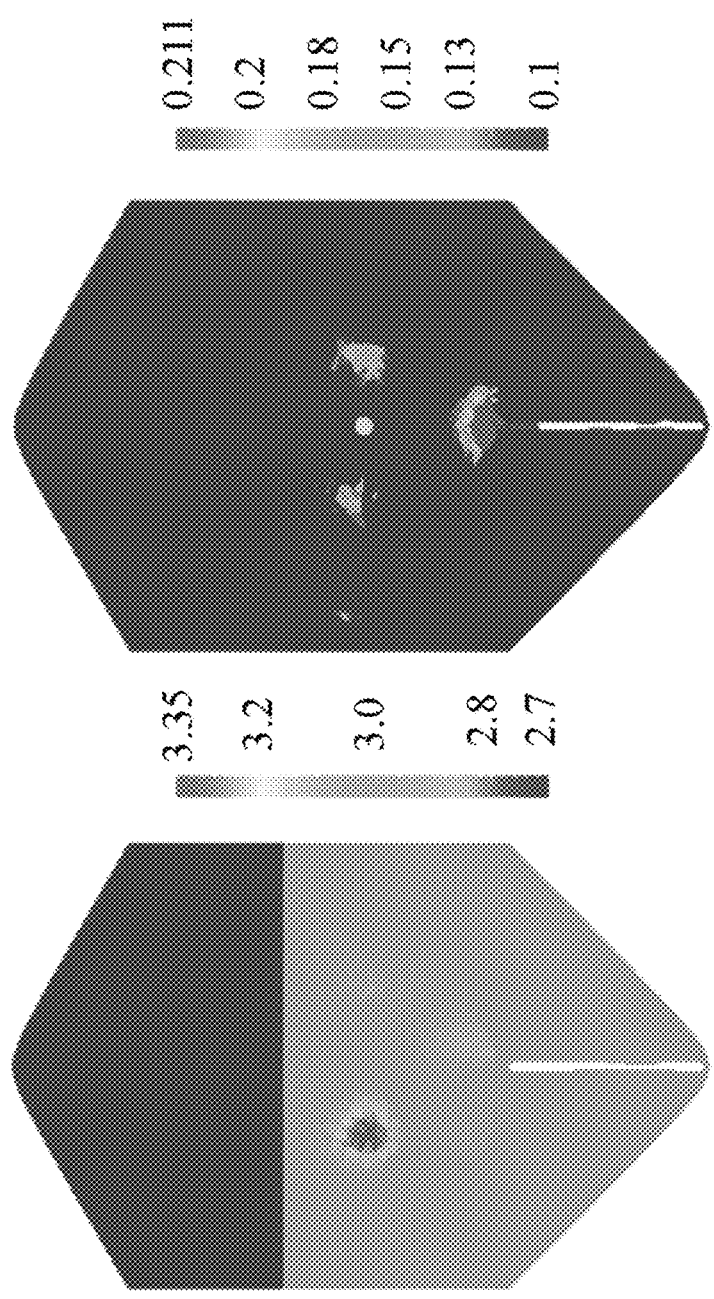

The simulated-spoiled grain 334, e.g., a bucket, was buried between antenna columns 2 and 3 but deeper than as imaged in FIGS. 25-26. The YZ plane for the real part (left image) and the imaginary part (right image) and the XZ plane for the real part (left image) and the imaginary part (right image) of an exemplary image reconstruction for the simulated-spoiled grain 334 buried between antenna columns 2 and 3 is shown in FIGS. 27-28, respectively.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A system for use in imaging an object using microwave tomography, wherein the system comprises:
   a plurality of antenna assemblies positionable about an object, wherein each antenna assembly of the plurality of antenna assemblies comprises at least one reconfigurable antenna configurable in at least a transmit state, a receive state, and a passive state, wherein the at least one reconfigurable antenna of the plurality of antenna assemblies is configured to deliver electromagnetic energy to irradiate the object when in the transmit state resulting in scattered electromagnetic energy, wherein the at least one reconfigurable antenna of the plurality of antenna assemblies is configured to sample scattered electromagnetic energy when in the receive state, and wherein the at least one reconfigurable antenna of the plurality of antenna assemblies is configured to not perturb electromagnetic energy when in the passive state; and
   a processor coupled to the plurality of antenna assemblies, wherein the processor is configured to:
      deliver electromagnetic energy using at least antenna assembly of the plurality of antenna assemblies to irradiate the object resulting in scattered electromagnetic energy, wherein one or more of the at least one reconfigurable antenna of the at least one antenna assembly delivering electromagnetic energy is configured in the transmit state to deliver the electromagnetic energy,
      sample the scattered electromagnetic energy using at least one antenna assembly of the plurality of antenna assemblies, wherein one or more of the at least one reconfigurable antenna of the at least one antenna assembly sampling the scattered electromagnetic energy is configured in the receive state to sample the scattered electromagnetic energy,
      configure one or more remaining reconfigurable antennas of the plurality of antennas assemblies that are not configured in the transmit state or the receive state into the passive state, and
      reconstruct an image of the object based on the sampled scattered electromagnetic energy.

2. The system of claim 1, wherein the system further comprises boundary condition apparatus configured to present a boundary condition relative to the plurality of antenna assemblies and the object.

3. The system of claim 2, wherein the boundary condition presented by the boundary condition defines a measurement domain, wherein the at least one antenna of the plurality of antenna assemblies extends into the measurement domain.

4. The system of claim 2, wherein the boundary condition apparatus comprises a conductive enclosure.

5. The system of claim 4, wherein the object is grain, and wherein the conductive enclosure is configured to store grain.

6. The system of claim 4, wherein the conductive enclosure is configured to contain a low-loss fluid.

7. The system of claim 1, wherein the at least one reconfigurable antenna of the plurality of antenna assemblies comprises:
   a first reconfigurable antenna extending along a first axis and configured to deliver or sample electromagnetic energy of at least a first polarity; and
   a second reconfigurable antenna extending along a second axis and configured to deliver or sample electromagnetic energy of at least a second polarity,
   wherein the first axis is orthogonal to the second axis and the first polarity is different than the second polarity.

8. The system of claim 7, wherein the at least one reconfigurable antenna of the plurality of antenna assemblies comprises a third reconfigurable antenna extending along a third axis and configured to deliver or sample electromagnetic energy of at least a third polarity, wherein the first axis is orthogonal to the third axis and the second axis is orthogonal to the third axis, and wherein each of the first and second polarity is different than the third polarity.

9. The system of claim 1, wherein the at least one reconfigurable antenna of the plurality of antenna assemblies comprises:
   a plurality of conductive segments, and
   a plurality of switchable segments coupling the conductive segments, wherein the switchable segments are configurable between a conducting configuration and a non-conducting configuration, wherein the plurality of conductive segments are electrically coupled via the switchable segments when the switchable segments are configured in the conducting configuration, wherein the plurality of conductive segments are electrically isolated from one another when the switchable segments are configured in the non-conducting configuration,
   wherein the switchable segments are configured in the conducting configuration when the antenna is configured into each of the transmit state and receive state, wherein the switchable segments are configured in the non-conducting configuration when the antenna is configured in the passive state.

10. The system of claim 1, wherein each antenna assembly antennas of the plurality of antenna assemblies comprises at least one ground plane, wherein each antenna of the at least one antenna is mounted to a different ground plane of the at least one ground plane.

11. The system of claim 1, wherein configuring one or more remaining reconfigurable antennas of the plurality of antennas assemblies that are not configured in the transmit state or the receive state into the passive state comprises configuring all of the remaining reconfigurable antennas of the plurality of antennas assemblies that are not configured in the transmit state or the receive state into the passive state.

12. The system of claim 1, wherein the at least one reconfigurable antenna of the plurality of antenna assemblies is further configurable in a probe state, wherein the at least one reconfigurable antenna of the plurality of antenna assemblies is configured to interact with the electromagnetic energy when in the probe state, wherein the processor is further configured to execute interacting with the scattered electromagnetic energy using at least one antenna assembly of the plurality of antenna assemblies, wherein one or more of the at least one reconfigurable antenna of the at least one antenna assembly interacting with the scattered electromagnetic energy is configured in the probe state to interact with the scattered electromagnetic energy.

13. The system of claim 12, wherein interacting with the scattered electromagnetic energy using at least one antenna assembly of the plurality of antenna assemblies further comprises individually configuring each of the at least one reconfigurable antenna of the plurality of antenna assemblies into the probe state that is not configured in the transmit state or the receive state until every antenna of the at least one reconfigurable antenna of the plurality of antenna assemblies has been individually configured into the probe state.

14. The system of claim 1, wherein delivering electromagnetic energy using at least one antenna assembly of the plurality of antenna assemblies to irradiate the object resulting in scattered electromagnetic energy comprises individually delivering electromagnetic energy with each of the at least one reconfigurable antenna of the plurality of antenna assemblies until every antenna of the at least one reconfigurable antenna of the plurality of antenna assemblies has individually delivered electromagnetic energy.

15. The system of claim 1, wherein sampling the scattered electromagnetic energy using at least one antenna assembly of the plurality of antenna assemblies comprises individually sampling electromagnetic energy with each antenna of the at least one reconfigurable antenna of the plurality of antenna assemblies until every antenna of the at least one reconfigurable antenna of the plurality of antenna assemblies has individually sampled the scattered electromagnetic energy.

16. The system of claim 1, wherein the reconstructed image is a quantitative image.

17. The system of claim 1, wherein the plurality of antenna assemblies are positioned in three dimensions with respect to the object.

18. The system of claim 1, wherein each antenna assembly of the plurality of antenna assemblies is in a fixed position relative to the object.

19. The system of claim 1, wherein each of the at least one reconfigurable antenna of the plurality of antenna assemblies is stationary with respect to each other.

20. A method of imaging an object using microwave tomography, wherein the method comprises:
   providing a plurality of antenna assemblies positionable about an object, wherein each antenna assembly of the plurality of antenna assemblies comprises at least one reconfigurable antenna, wherein the at least one reconfigurable antenna of the plurality of antenna assemblies is configurable in at least a transmit state, a receive state, and a passive state, wherein the at least one reconfigurable antenna of the plurality of antenna assemblies is configured to deliver electromagnetic energy to irradiate the object when in the transmit state resulting in scattered electromagnetic energy, wherein the at least one reconfigurable antenna of the plurality of antenna assemblies is configured to sample scattered electromagnetic energy when in the receive state, and wherein the at least one reconfigurable antenna of the plurality of antenna assemblies is configured to not perturb electromagnetic energy when in the passive state;
   delivering electromagnetic energy using at least one antenna assembly of the plurality of antenna assemblies to irradiate the object resulting in scattered electromagnetic energy, wherein one or more of the at least one reconfigurable antenna of the at least one antenna assembly delivering electromagnetic energy is configured in the transmit state to deliver the electromagnetic energy;

sampling the scattered electromagnetic energy using at least one antenna assembly of the plurality of antenna assemblies, wherein one or more of the at least one reconfigurable antenna of the at least one antenna assembly sampling the scattered electromagnetic energy is configured in the receive state to sample the scattered electromagnetic energy;

configuring one or more remaining reconfigurable antennas of the plurality of antenna assemblies that are not configured in the transmit state or the receive state into the passive state; and reconstructing an image of the object based on the sampled scattered electromagnetic energy.

21. The method of claim 20, wherein the method further comprises providing boundary condition apparatus configured to present a boundary condition relative to the plurality of antenna assemblies and the object.

22. The method of claim 20, wherein the at least one reconfigurable antenna of the plurality of antenna assemblies comprises:
 a first reconfigurable antenna extending along a first axis and configured to deliver or sample electromagnetic energy of at least a first polarity; and
 a second reconfigurable antenna extending along a second axis and configured to deliver or sample electromagnetic energy of at least a second polarity,
 wherein the first axis is orthogonal to the second axis and the first polarity is different than the second polarity.

23. The method of claim 20, wherein the at least one reconfigurable antenna of the plurality of antenna assemblies comprises:
 a plurality of conductive segments, and
 a plurality of switchable segments coupling the conductive segments, wherein the switchable segments are configurable between a conducting configuration and a non-conducting configuration, wherein the plurality of conductive segments are electrically coupled via the switchable segments when the switchable segments are configured in the conducting configuration, wherein the plurality of conductive segments are electrically isolated from one another when the switchable segments are configured in the non-conducting configuration,
 wherein the switchable segments are configured in the conducting configuration when the antenna is configured into each of the transmit state and receive state, wherein the switchable segments are configured in the non-conducting configuration when the antenna is configured in the passive state.

24. The method of claim 20, wherein each antenna assembly antennas of the plurality of antenna assemblies comprises at least one ground plane, wherein each antenna of the at least one antenna is mounted to a different ground plane of the at least one ground plane.

25. The method of claim 20, wherein configuring one or more remaining reconfigurable antennas of the plurality of antennas assemblies that are not configured in the transmit state or the receive state into the passive state comprises configuring all of the remaining reconfigurable antennas of the plurality of antennas assemblies that are not configured in the transmit state or the receive state into the passive state.

26. The method of claim 20, wherein the at least one reconfigurable antenna of the plurality of antenna assemblies is further configurable in a probe state, wherein the at least one reconfigurable antenna of the plurality of antenna assemblies is configured to interact with the electromagnetic energy when in the probe state, wherein method further comprises interacting with the scattered electromagnetic energy using at least one antenna assembly of the plurality of antenna assemblies, wherein one or more of the at least one reconfigurable antenna of the at least one antenna assembly interacting with the scattered electromagnetic energy is configured in the probe state to interact with the scattered electromagnetic energy.

27. The method of claim 26, wherein interacting with the scattered electromagnetic energy using at least one antenna assembly of the plurality of antenna assemblies further comprises individually configuring each of the at least one reconfigurable antenna of the plurality of antenna assemblies into the probe state that is not configured in the transmit state or the receive state until every antenna of the at least one reconfigurable antenna of the plurality of antenna assemblies has been individually configured into the probe state.

28. The method of claim 20, wherein delivering electromagnetic energy using at least one antenna assembly of the plurality of antenna assemblies to irradiate the object resulting in scattered electromagnetic energy comprises individually delivering electromagnetic energy with each of the at least one reconfigurable antenna of the plurality of antenna assemblies until every antenna of the at least one reconfigurable antenna of the plurality of antenna assemblies has individually delivered electromagnetic energy.

29. The method of claim 20, wherein sampling the scattered electromagnetic energy using at least one antenna assembly of the plurality of antenna assemblies comprises individually sampling electromagnetic energy with each antenna of the at least one reconfigurable antenna of the plurality of antenna assemblies until every antenna of the at least one reconfigurable antenna of the plurality of antenna assemblies has individually sampled the scattered electromagnetic energy.

30. The method of claim 20, wherein the reconstructed image is a quantitative image.

31. The method of claim 20, wherein the plurality of antenna assemblies are positioned in three dimensions with respect to the object.

32. The method of claim 20, wherein each antenna assembly of the plurality of antenna assemblies is in a fixed position relative to the object.

33. The method of claim 20, wherein each of the at least one reconfigurable antenna of the plurality of antenna assemblies is stationary with respect to each other.

* * * * *